US009091655B2

(12) United States Patent
McLaughlin et al.

(10) Patent No.: US 9,091,655 B2
(45) Date of Patent: Jul. 28, 2015

(54) PHOTOLUMINESCENCE QUANTUM YIELD (PLQY) TEST OF QUANTUM DOT (QD) FILMS

(71) Applicants: Nathan McLaughlin, Portland, OR (US); Jason King, San Francisco, CA (US); Michael Jansen, Palo Alto, CA (US)

(72) Inventors: Nathan McLaughlin, Portland, OR (US); Jason King, San Francisco, CA (US); Michael Jansen, Palo Alto, CA (US)

(73) Assignee: Pacific Light Technologies Corp., Portland, OR (US)

( * ) Notice: Subject to any disclaimer, the term of this patent is extended or adjusted under 35 U.S.C. 154(b) by 0 days.

(21) Appl. No.: 14/205,040

(22) Filed: Mar. 11, 2014

(65) Prior Publication Data

US 2014/0264073 A1 Sep. 18, 2014

Related U.S. Application Data

(60) Provisional application No. 61/778,114, filed on Mar. 12, 2013.

(51) Int. Cl.
*G01N 21/64* (2006.01)
*G01J 3/443* (2006.01)

(52) U.S. Cl.
CPC .............. *G01N 21/6489* (2013.01); *G01J 3/443* (2013.01)

(58) Field of Classification Search
CPC ......... G01J 3/443; G01J 1/58; G01N 21/6489
USPC ...................................... 250/458.1
See application file for complete search history.

(56) References Cited

U.S. PATENT DOCUMENTS

| 7,326,365 | B2* | 2/2008 | Bawendi et al. ........ 252/301.4 R |
| 2001/0000279 | A1* | 4/2001 | Daniels et al. .................. 73/105 |
| 2011/0155926 | A1* | 6/2011 | Ohkubo ..................... 250/459.1 |
| 2012/0327209 | A1* | 12/2012 | Folling ............................ 348/79 |
| 2013/0112941 | A1* | 5/2013 | Kurtin et al. ..................... 257/13 |
| 2013/0112942 | A1* | 5/2013 | Kurtin et al. .................... 257/13 |
| 2014/0049155 | A1* | 2/2014 | Kurtin ........................... 313/512 |
| 2014/0117311 | A1* | 5/2014 | Kurtin ............................ 257/22 |

OTHER PUBLICATIONS

Laurent Porres, et al. "Absolute Measurements of Photoluminescence Quantum Yields of Solutions Using an Integrating Sphere", *Journal of Fluorescence*, (2006), pp. 267-273.

* cited by examiner

*Primary Examiner* — Kiho Kim
(74) *Attorney, Agent, or Firm* — Blakely, Sokoloff, Taylor & Zafman

(57) ABSTRACT

Photoluminescence quantum yield (PLQY) testing of quantum dots is described. In one embodiment, a method involves heating a sample including quantum dots and illuminating the sample with a light source. The method involves measuring spectra of luminescence from the illuminated quantum dots of the sample at each of a plurality of temperatures. The method involves measuring each of the plurality of temperatures with a temperature sensor. The PLQY at each of the plurality of temperatures is computed based on the measured spectra. The method further involves computing a relationship between QD emission wavelength of the measured spectra and the plurality of temperatures measured with the temperature sensor. The relationship is used to determine the QD temperature corresponding to each of the PLQY computations. In one embodiment, an integrating sphere moves on a gantry over the samples.

33 Claims, 15 Drawing Sheets

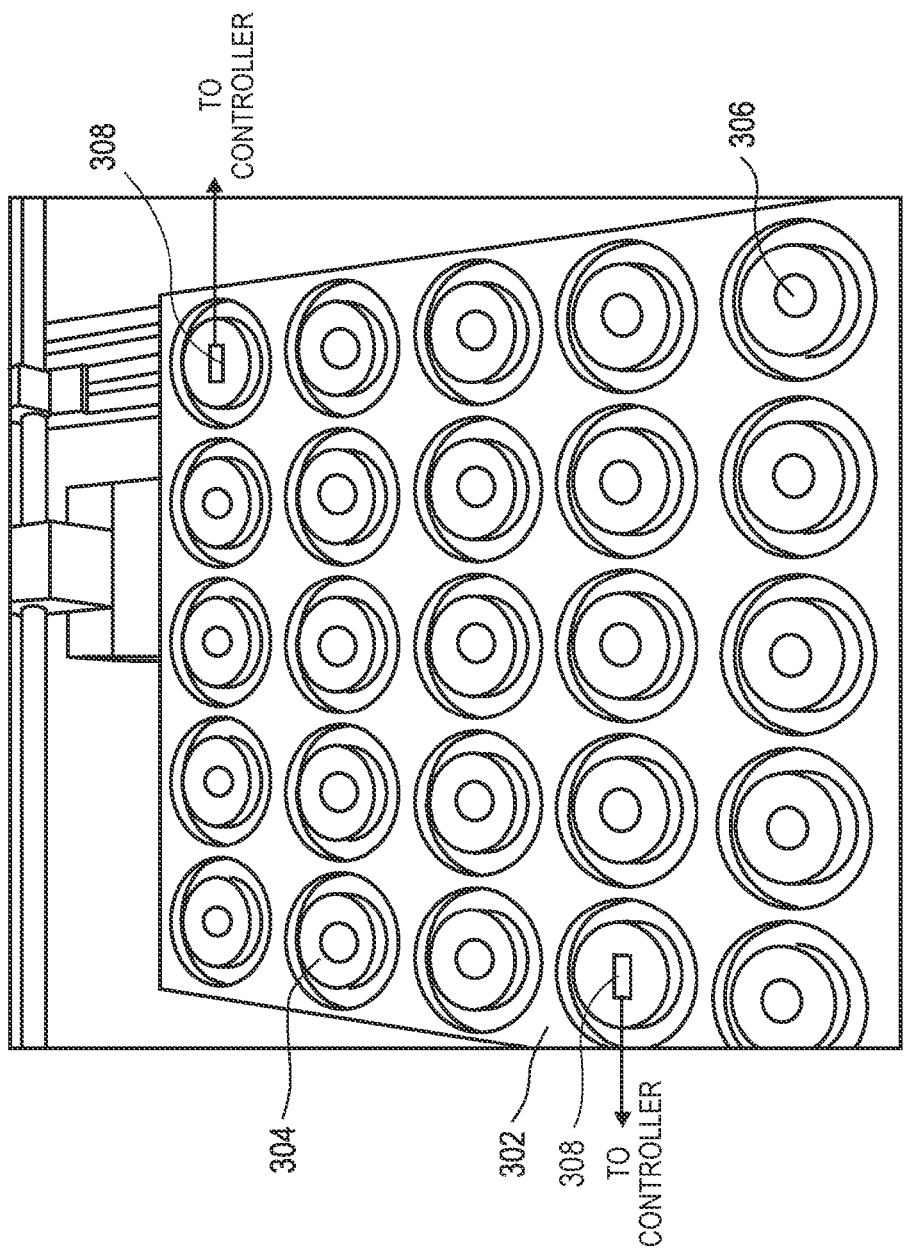

US 9,091,655 B2

PHOTOLUMINESCENCE QUANTUM YIELD (PLQY) TEST OF QUANTUM DOT (QD) FILMS

CROSS-REFERENCE TO RELATED APPLICATIONS

This application claims the benefit of U.S. Provisional Application No. 61/778,114, filed Mar. 12, 2013, the entire contents of which are hereby incorporated by reference herein.

TECHNICAL FIELD

Embodiments of the present invention are in the field of quantum dots and, in particular, testing of photoluminescence quantum yield (PLQY) of quantum dots.

BACKGROUND

Quantum dots having a high photoluminescence quantum yield (PLQY) may be applicable as down-converting materials in down-converting nano-composites used in solid state lighting applications. Down-converting materials are used to improve the performance, efficiency and color choice in lighting applications, particularly light emitting diodes (LEDs). In such applications, quantum dots absorb light of a particular first (available or selected) wavelength, usually blue, and then emit light at a second wavelength, usually red or green.

Testing of quantum dot films may be performed to determine the photoluminescence quantum yield (PLQY) of the quantum dot films. Some existing methods of determining PLQY, referred to as "relative methods," assume that the sample absorbance does not vary with temperature, which may be inaccurate. Other methods, referred to as "absolute methods," may allow for temperature to be taken into account when determining PLQY. However, the "absolute methods" of determining PLQY can be prohibitively time-consuming.

SUMMARY

Embodiments of the present invention include systems and methods for testing photoluminescence quantum yield (PLQY) of quantum dots.

In one embodiment, a method involves heating a sample including quantum dots. The method involves illuminating the sample with a light source and measuring spectra of luminescence from the illuminated quantum dots of the sample at each of a plurality of temperatures. The method involves measuring each of the plurality of temperatures with a temperature sensor, and computing the PLQY at each of the plurality of temperatures based on the measured spectra. The method involves computing a relationship between quantum dot (QD) emission wavelength of the measured spectra and the plurality of temperatures measured with the temperature sensor. The relationship is used to determine the QD temperature corresponding to each of the PLQY computations.

In another embodiment, the method involves moving an integrating sphere on a gantry over the plurality of samples including quantum dots. The method involves illuminating a given sample over which the integrating sphere is disposed with a light source coupled with the gantry. The method involves measuring spectra of luminescence from the quantum dots of the given sample at a plurality of temperatures. The integrating sphere moves on the gantry over another sample in between measurements at different temperatures. The method also involves determining the PLQY for the plurality of samples at the plurality of temperatures based on the measured spectra.

According to one embodiment, a system for testing PLQY of quantum dots includes a stage to support a sample including the quantum dots and a heater to heat the sample to a plurality of temperatures. The system further includes a light source to illuminate the sample. A spectrometer measures spectra of luminescence from the illuminated quantum dots at the plurality of temperatures, and a temperature sensor measures a temperature of the sample corresponding to the measured spectra. The system includes a computing device to compute: the PLQY at the plurality of temperatures based on the measured spectra, a relationship between quantum dot (QD) emission wavelength of the measured spectra and the plurality of temperatures measured with the temperature sensor, and a QD temperature corresponding to each of the PLQY computations based on the relationship between the QD emission wavelength and the plurality of temperatures measured with the temperature sensor.

In another embodiment, a system for testing PLQY of quantum dots includes an integrating sphere coupled with a gantry. An electronic memory stores coordinates of the plurality of samples relative to the gantry. The integrating sphere is configured to move on the gantry over the plurality of samples based on the coordinates. The system includes a light source coupled with the integrating sphere to illuminate a given sample over which the integrating sphere is disposed. A spectrometer is also coupled with the integrating sphere to measure spectra of luminescence from the given sample at a plurality of temperatures. The integrating sphere is configured to move on the gantry over another sample in between measurements at different temperatures. The system also includes a computing device to determine the PLQY for the plurality of samples at the plurality of temperatures based on the measured spectra.

BRIEF DESCRIPTION OF THE DRAWINGS

Embodiments of the present invention are illustrated by way of example, and not limitation, in the figures of the accompanying drawings in which:

FIG. 3 is a top-down view of a stage with quantum-dot containing samples, in accordance with an embodiment of the present invention.

DETAILED DESCRIPTION

Photoluminescence quantum yield (PLQY) testing methods for quantum dots are described herein. In the following description, numerous specific details are set forth, such as specific quantum dot geometries and efficiencies, in order to provide a thorough understanding of embodiments of the present invention. It will be apparent to one skilled in the art that embodiments of the present invention may be practiced without these specific details. In other instances, well-known related apparatuses, such as the host of varieties of applicable light emitting diodes (LEDs), are not described in detail in order to not unnecessarily obscure embodiments of the present invention. Furthermore, it is to be understood that the various embodiments shown in the figures are illustrative representations and are not necessarily drawn to scale.

Figure 1:
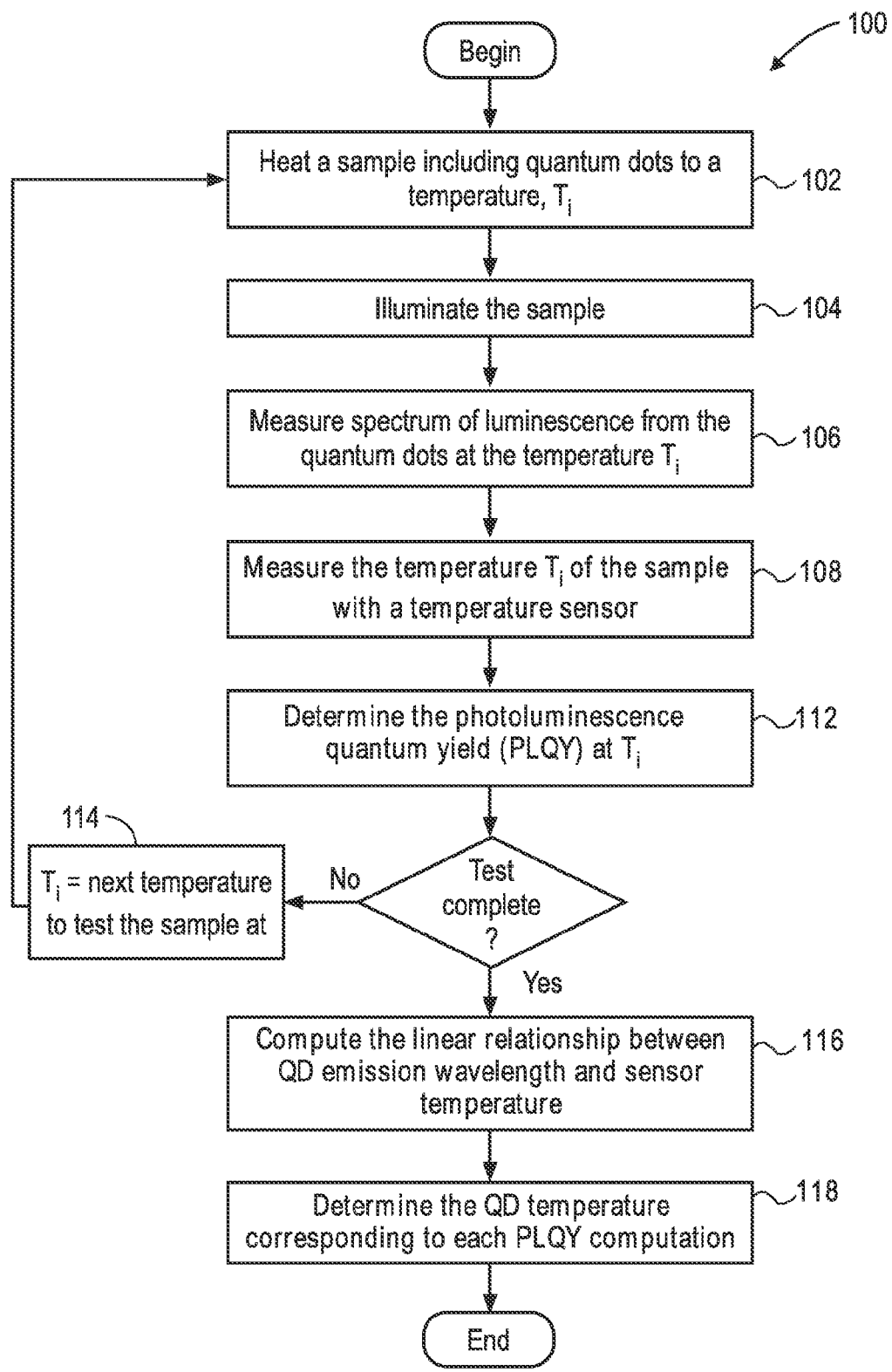
FIG. 1 is a flow diagram illustrating a method of testing photoluminescence quantum yield (PLQY) of quantum dots, in accordance with an embodiment of the present invention.
Figure 2:
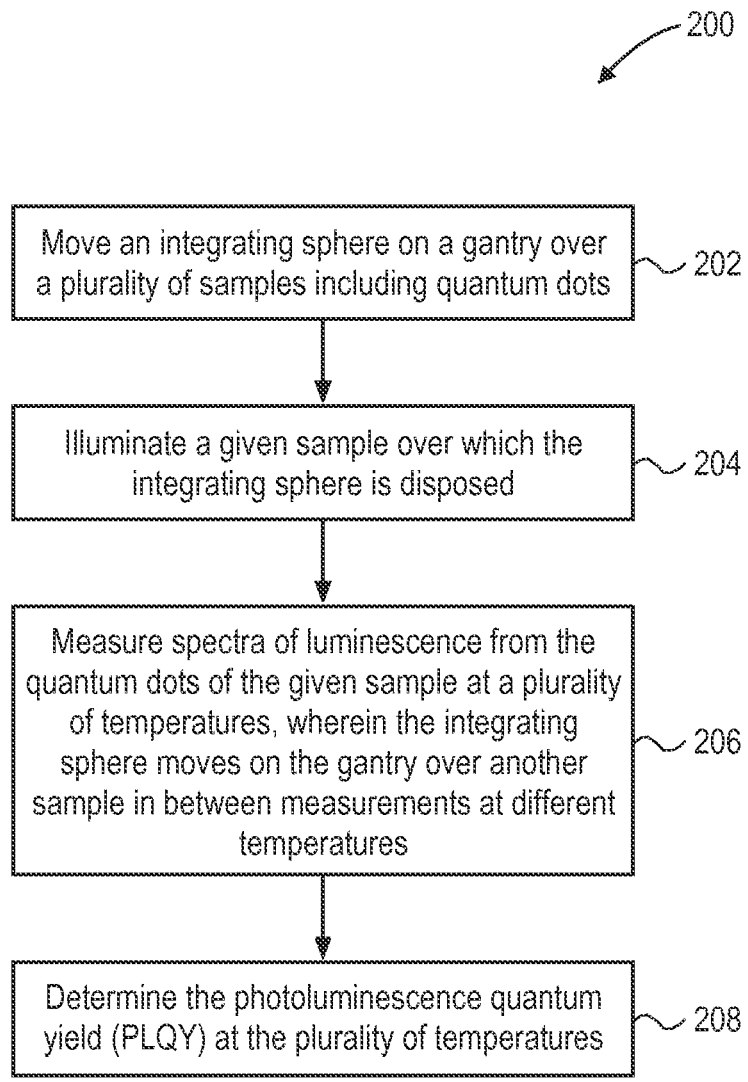
FIG. 2 is a flow diagram illustrating a method of testing PLQY of quantum dots, in accordance with an embodiment of the present invention.

One or more embodiments described herein are directed to high throughput testing of PLQY of quantum dot films as a function of temperature. FIGS. 1 and 2 are flow diagrams illustrating methods of testing PLQY of quantum dots, in accordance with embodiments of the present invention. The method 100 of FIG. 1 involves determining what the actual quantum dot (QD) temperature was during the measurements based on the shift in quantum dot emission peak wavelength with sensor temperature, in accordance with an embodiment of the present invention. The method 100 involves heating a sample including the quantum dots, at operation 102. A sample may include, for example, a film with quantum dots, such as the quantum dots described below with respect to FIGS. 7-10. According to one embodiment, heating the sample involves heating a stage over which the sample is disposed. For example, the method may further involve supporting the sample over a heated stage. Supporting the sample over the stage may further involve supporting the sample over a diffusely reflective solid material, and supporting the diffusely reflective solid material with the sample over the stage. FIG. 3, which is discussed below, illustrates an example of a stage 302 over which samples are disposed. Heating the sample may involve heating the sample to a plurality of specific predetermined temperatures to enable testing the PLQY as a function of temperature. In one embodiment, the method involves heating the sample from approximately 19° C. to 120° C. In one such example, the sample is brought to and tested at a plurality of temperatures within the testing range.

The method 100 also involves illuminating the sample with a light source, at operation 104. For example, in one embodiment involving the use of an integrating sphere, illuminating the sample involves illuminating the sample with the light source coupled with the integrating sphere (e.g., through a port in the integrating sphere). A system with an integrating sphere is discussed in further detail below with respect to FIGS. 4A, 4B, and 5. The light source may include, for example, a laser or LED, such as described in the examples below.

At operation 106, the method involves measuring spectra of luminescence from the illuminated quantum dots at the current temperature, $T_i$. In an embodiment involving the use of an integrating sphere, measuring the spectra may involve measuring the spectra with a spectrometer coupled with the integrating sphere. In one embodiment, the measurement process is continuous. Embodiments may involve any number of measurements per temperature cycle, and in one embodiment, measurements are concentrated at the higher end of the temperature range.

The method 100 also involves measuring the temperature of the sample with a temperature sensor during the spectra measurement, at operation 108. The temperature sensor may be a thermocouple, or other temperature sensor capable of measuring the temperature of the sample or nearby material. In one embodiment, the temperature sensor may be supported over the stage (e.g., embedded in, on, or disposed over the stage) and adjacent to the sample (e.g., located near enough to the sample to provide a sufficiently accurate temperature measurement). In one such embodiment, the temperature sensor is embedded in the same type of material as the sample. Thus, the material that the temperature sensor is embedded in experiences a same or similar rate of heating as the sample, enabling accurate temperature measurements of the sample.

The method 100 continues at operation 112 with determining the PLQY at the current temperature based on the measured spectra. If stopping criteria are encountered (e.g., if the test has been performed at all desired temperatures, or some other stopping criteria is encountered), the test is terminated. If stopping criteria are not reached, the method 100 continues at operation 114, by determining the next temperature to heat the sample to. The method 100 then repeats operation 102-112 until completion of the test.

If the test is complete (e.g., if measurements have been performed at all desired temperatures), the method 100 continues at operation 116 by computing the linear relationship between QD emission wavelength and sensor temperature. Determining the relationship between QD emission wavelength and sensor temperature may involve, for example, fitting a line to the data set made up of the peak wavelength of each measured emission and the corresponding measured temperature during the time of that emission. In one embodiment, determining the shift in quantum dot emission peak wavelength with temperature involves weighting temperature measurements in a predetermined range to have greater significance. For example, measurements made between 19-65° C. may be weighted to have more significance in determining the peak shift due to larger sensor uncertainty at higher temperatures (e.g., larger uncertainty in the temperature measurements that are greater than 65° C.). The method then involves using this relationship to determine the QD temperature corresponding to each PLQY computation, at operation 118. Other weighting schemes may be used (e.g., based on test parameters and the reliability of the temperature sensors used to measure the sample temperature).

Thus, the method 100 involves measuring sample temperature and spectra of luminescence from the illuminated quantum dots of the sample at each of a plurality of temperatures. The PLQY is computed based on the measured spectra, and the QD emission peak shift is used to determine the QD temperature for each PLQY computation.

FIG. 2 is a flow diagram illustrating a method of testing photoluminescence quantum yield of quantum dots using an automated gantry system, in accordance with an embodiment of the present invention. The method 200 involves moving an integrating sphere on a gantry over the plurality of samples including quantum dots, at operation 202. As is discussed in more detail below with respect to FIGS. 4A and 4B, the gantry may be a three-axis gantry on which the integrating sphere moves.

In one embodiment, the samples are supported over one or more stages, and moving the integrating sphere over a sample involves moving the integrating sphere over a stage over which the sample is disposed. For example, the method 200 may further involve supporting a plurality of samples over diffusely reflective solid material, and supporting the diffusely reflective solid material with the plurality of samples over one or more stages. In one such embodiment, the interior surface of the integrating sphere may be the same or similar to a coating of diffusely reflective solid material over which the plurality of samples are supported. In one embodiment, the system stores coordinates of the samples (or stage) relative to the gantry, and movement of the integrating sphere on the gantry is based on stored coordinates of the plurality of samples relative to the gantry.

At operation 204, the method involves illuminating a given sample over which the integrating sphere is disposed with a light source coupled with the gantry. As discussed above with respect to the method 100 of FIG. 1, illuminating a given sample involves illuminating the given sample with a laser or LED. The method 200 also involves measuring spectra of luminescence from the quantum dots of the given sample at a plurality of temperatures, at operation 206. Measuring the temperature dependence of a single sample may take a significant amount of time (e.g., several hours). Most of the time involved in measuring temperature dependence does not involve measurement, but instead involves temperature ramping and thermal stabilization of the sample. According to embodiments, the integrating sphere moves on the gantry over another sample in between measurements at different temperatures. Thus, the use of the automated gantry system allows the integrating sphere to leave a measurement position during inactive times (e.g., while a sample is being heated) to be used on additional samples. Such embodiments eliminate the need for re-positioning samples during the entire heating and measurement period.

The method 200 further involves determining the PLQY for the plurality of samples at the plurality of temperatures based on the measured spectra at operation 208. Thus, the method 200 of FIG. 2 enables determining PLQY for a plurality of samples at a plurality of temperatures without re-positioning the sample, which can enable high throughput testing of PLQY.

According to embodiments, the techniques of both the method 100 of FIG. 1 and the method 200 of FIG. 2 are used to test the PLQY of quantum dots. For example, the method 100 of FIG. 1 may further involve the use of an integrating sphere coupled with a gantry. In one such embodiment, the method 100 may include storing coordinates of the gantry over the sample, and while the sample is being heated to the next temperature, moving the integrating sphere on the gantry over another sample. After taking measurements for the other sample, the integrating sphere may be moved on the gantry back over the previous sample based on the stored coordinates. In another example, the method 200 may involve determining the temperature of a given sample that is expected to be outside a predetermined temperature range based on the QD emission peak shift.

FIGS. 3, 4A, 4B, and 5 illustrate a system for PLQY of quantum dots, in accordance with an embodiment of the invention. FIG. 3 is a top-down view of a stage with quantum-dot containing samples, in accordance with an embodiment of the present invention. The stage 302 may be a heated stage, configured to be heated to a plurality of temperatures. Any appropriate heating element may be used to heat the stage 302 (e.g., in a temperature range of 19-120° C.). A diffusely reflective solid material 304 is disposed over the stage to support samples 306. The reflective solid material 304 may be machined to a desired configuration and attached to the stage 302. In an embodiment using an integrating sphere, the sample may be supported over the same (or similar) diffusely reflective solid material as an interior coating of the integrating sphere.

In one embodiment, the reflective solid material 304 may be heated (e.g., via the heated stage 302) without deformation or discoloration, enabling measurements to be made while the stage 302 is hot. The internal temperature of the samples 306 may be measured using one or more thermocouples 308 in, on, or over the stage. For example, in the illustrated embodiment, two thermocouples 308 are embedded in the same type of material as the sample and sitting in adjacent locations on the stage 302. Other embodiments may involve other types and/or configurations of temperature sensors. For example, other embodiments may involve less than or more than the number of temperature sensors depicted in FIG. 3. As described above with respect to the method 100 of FIG. 1, the temperature sensor(s) may be used to measure the temperature of the sample corresponding to measured spectra if the temperature is expected to be within a predetermined range. Temperature measurements may be sent to a computing device such as the controllers 410 in FIG. 4B or other computer device. A "controller" as referred to herein may include hardware, software, or a combination of hardware and software and may be configured to receive information (e.g., measurements, parameters, etc.), store information, control elements of the testing equipment (e.g., to heat the stage 302), to perform computations, and/or to communicate with other computing devices. A controller or other computing device may include some or all of the elements described below with respect to FIG. 18.

Figure 4A:
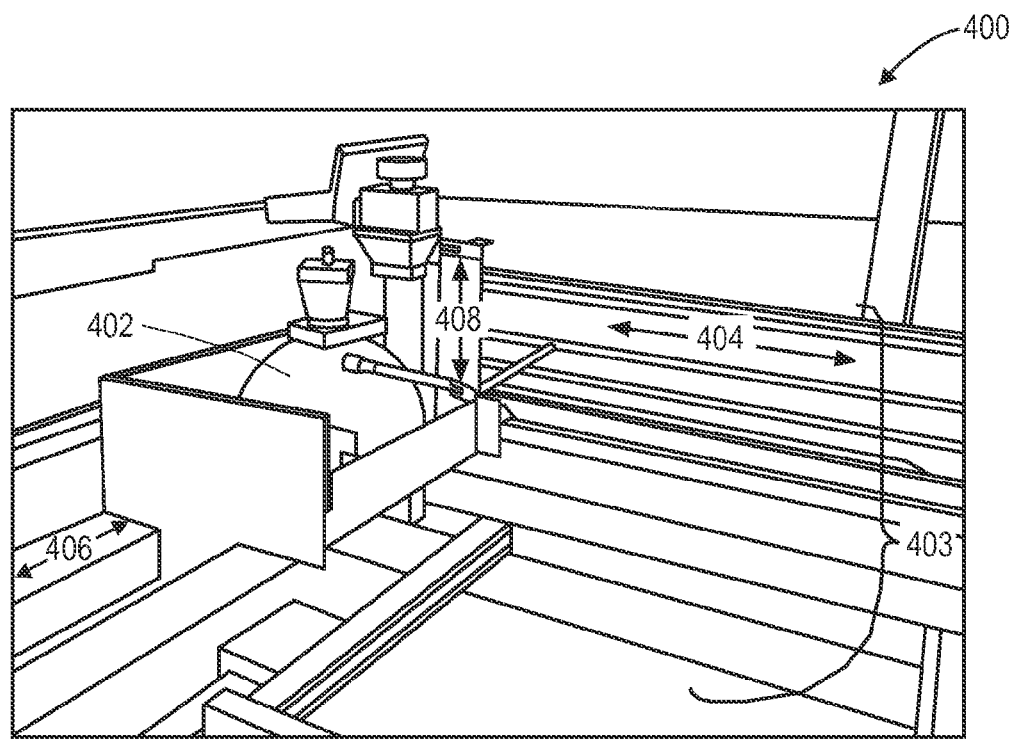
FIGS. 4A and 4B are illustrations of a system for testing photoluminescence quantum yield of quantum dots, including an integrating sphere coupled with a gantry, in accordance with embodiments of the present invention.
Figure 4B:
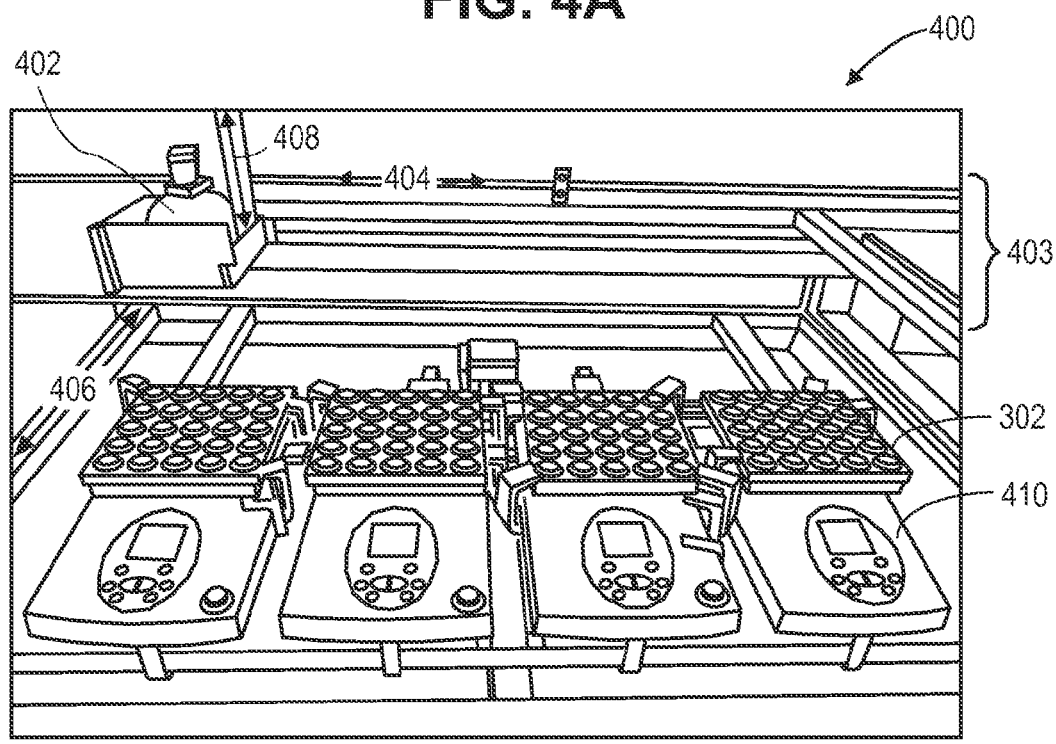

FIGS. 4A and 4B are illustrations of a system 400 for testing photoluminescence quantum yield of quantum dots, including an integrating sphere 402 coupled with a gantry 403, in accordance with embodiments of the present invention. In the illustrated embodiment, the gantry comprises three axes 404, 406, and 408 along which the integrating sphere is configured to move. Thus, the integrating sphere 402 is configured to move on the gantry 403 over a plurality of samples disposed over stages 302. For example, four stages 302 are illustrated in FIG. 4B. In one embodiment, the integrating sphere 402 is configured to be lowered over a first stage on one axis 408 (e.g., a vertical axis) of the gantry 403. After testing the samples on the first stage at one temperature, the integrating sphere is raised from the first stage on the axis 408, and moved along the axis 404 (e.g., a horizontal axis) over another stage. While the samples on the first stage are being heated to a next temperature, the samples on the other stage can be tested. Although a single row of stages 302 is illustrated, other embodiments may involve a configuration of samples such that the integrating sphere also moves along the axis 406. Moving the integrating sphere on the gantry enables measurements for a large number of samples (e.g., 180 samples or more) to be performed at each temperature. Thus, embodiments enable faster and more efficient testing of samples, which may be desirable for high throughput manufacturing environments.

According to an embodiment, the system 400 also includes an electronic memory to store coordinates of the plurality of samples relative to the gantry. The integrating sphere 402 is configured to move on the gantry 403 over the plurality of samples based on the coordinates. In the illustrated example with a three-axis gantry, storing coordinates may involves storing a location corresponding to each axis (e.g., x, y, and z coordinates). Other embodiments may use a gantry with more or less than three axes. The stored coordinates enable the gantry 403 to position the integrating sphere 402 in the same position during each measurement of a sample. A computing device stores measurements as well as the coordinates at which the measurements were taken, and associates the measurements with the sample at those coordinates.

Figure 5:
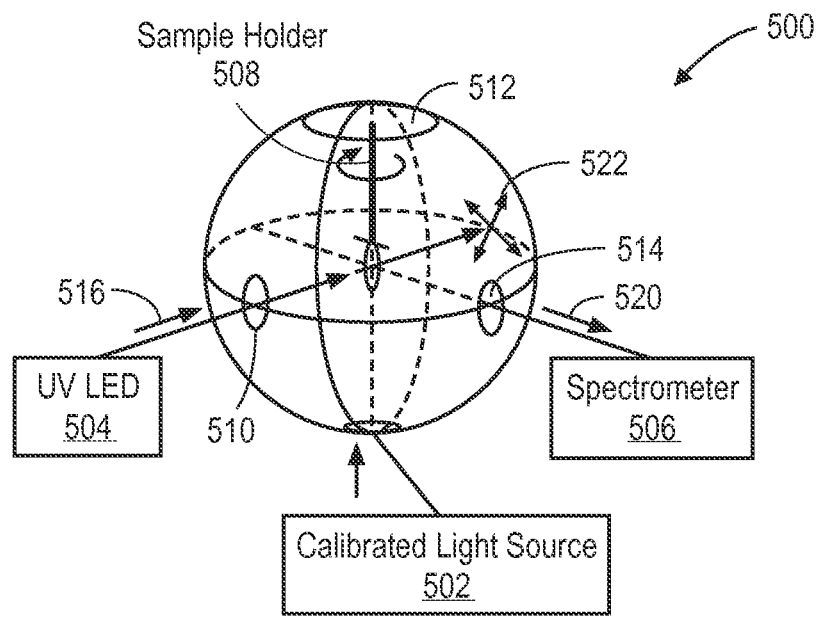
FIG. 5 is an isometric view of an integrating sphere, in accordance with embodiments of the present invention.

The measurements of PLQY may be performed according to the method disclosed in "Absolute Measurements of Photoluminescence Quantum Yields of Solutions Using an Integrating Sphere," Laurent Porres et al., Journal of Fluorescence, Volume 16, Issue 2, pp 267-273 (2006), or according to any other technique for determining PLQY. For example, FIG. 5 illustrates a schematic of an integrating sphere 500 for measuring the PLQY, in accordance with an embodiment of the invention. The integrating sphere 500 includes a sample holder 508 to support a sample. A light source 504 is coupled with the integrating sphere to illuminate a given sample over which the integrating sphere is disposed with light 516. In the illustrated embodiment, the light source 504 is an ultra-violet (UV) LED, however, other light sources may be used, such as a laser. In one embodiment, the integrating sphere 500 is coated with a diffusely reflective material to uniformly scatter the light 516 as illustrated by the scattered light 522.

A spectrometer 506 is coupled with the integrating sphere 500 to measure spectra of luminescence 520 from a given sample at a plurality of temperatures. The integrating sphere may also be coupled with a calibrated light source 502 (e.g., to help identify errors in the measured spectra). In the illustrated embodiment, the light source 504 is coupled with the integrating sphere 500 via a first port 510 and the spectrometer 506 is coupled with the integrating sphere 500 via a second port 514 at 90 degrees relative to the light source port 510. The calibrated light source is coupled with the integrating sphere 500 via a third port 502. The integrating sphere 500 includes a fourth port 512 through which the sample holder 508 may be introduced to the integrating sphere 500. Other embodiments may include other numbers or configurations of ports. Measurement made with the spectrometer 506 and other parameters may be sent to a computing device to determine the PLQY for the plurality of samples at the plurality of temperatures based on the measured spectra. Other parameters which may be sent to the computing device include, for example, configurations of the light source 504, calibrated light source 502, sample holder 508, spectrometer 506, and/or coordinates of the current sample (or stage) with respect to the gantry.

In one embodiment, the PLQY is measured with a Labsphere™ 6" integrating sphere, a Labsphere™ LPS-200-0105 calibrated white light source, a 3.8 W, 405 nm Thorlabs™ M405L2 UV LED, and an Ocean Optics™ USB4000-VIS-NIR spectrometer. In one such embodiment, the spectrometer 506 and the UV LED 504 are coupled with the integrating sphere 500 using Ocean Optics™ UV-Vis optical fibers. The spectrometer fiber is attached to a lens in the port 514 at the side of the integrating sphere 500 at 90 degrees relative to the excitation source (e.g., 90 degrees relative to the UV LED 504 coupled with the integrating sphere via the port 510). In one embodiment, the lens is behind a flat baffle to ensure only diffuse light reaches the lens. The calibrated white light source is coupled with the port 502 in the side of the integrating sphere 500 at 90 degrees to both the excitation source port 510 and the spectrometer port 514.

Figure 6:
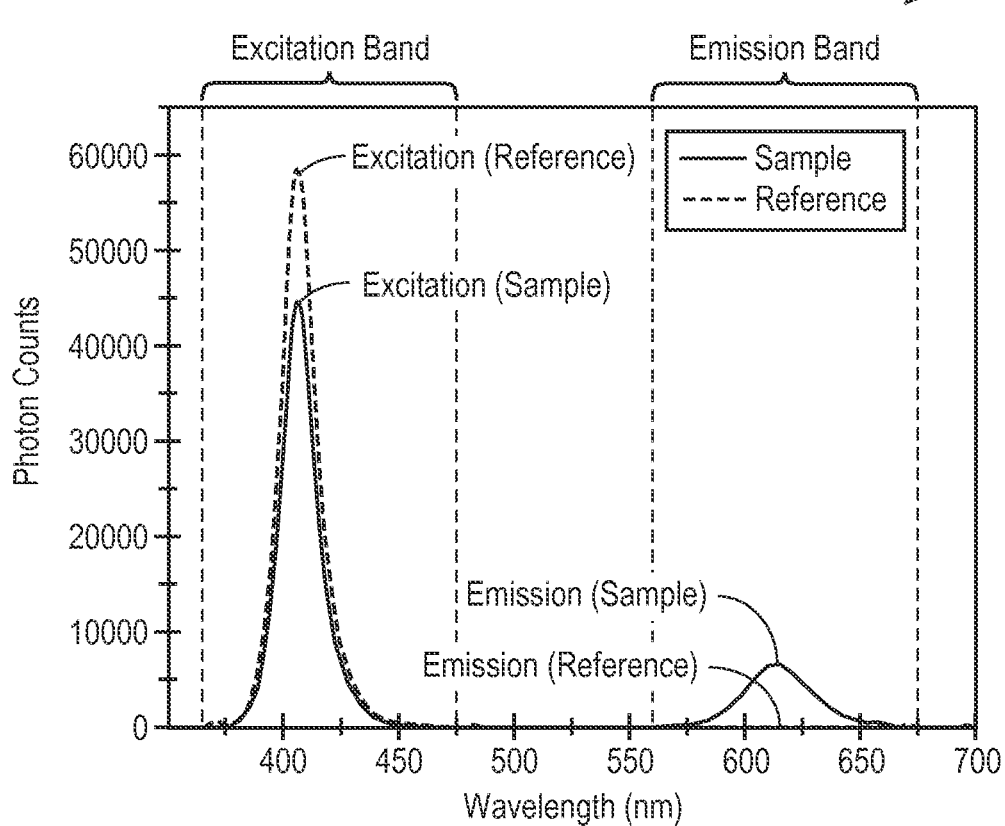
FIG. 6 is a plot of photon counts as a function of wavelength for a sample and reference emission spectra used in the measurement of photoluminescence quantum yield, in accordance with an embodiment of the present invention.

FIG. 6 is a plot 600 of photon counts as a function of wavelength (in nanometers) for a sample and reference emission spectra used in the measurement of photoluminescence quantum yield, in accordance with an embodiment of the present invention. Referring to the plot 600, both excitation and emission peaks for a sample are calibrated against corresponding excitation and emission peaks for a reference.

Figure 7:
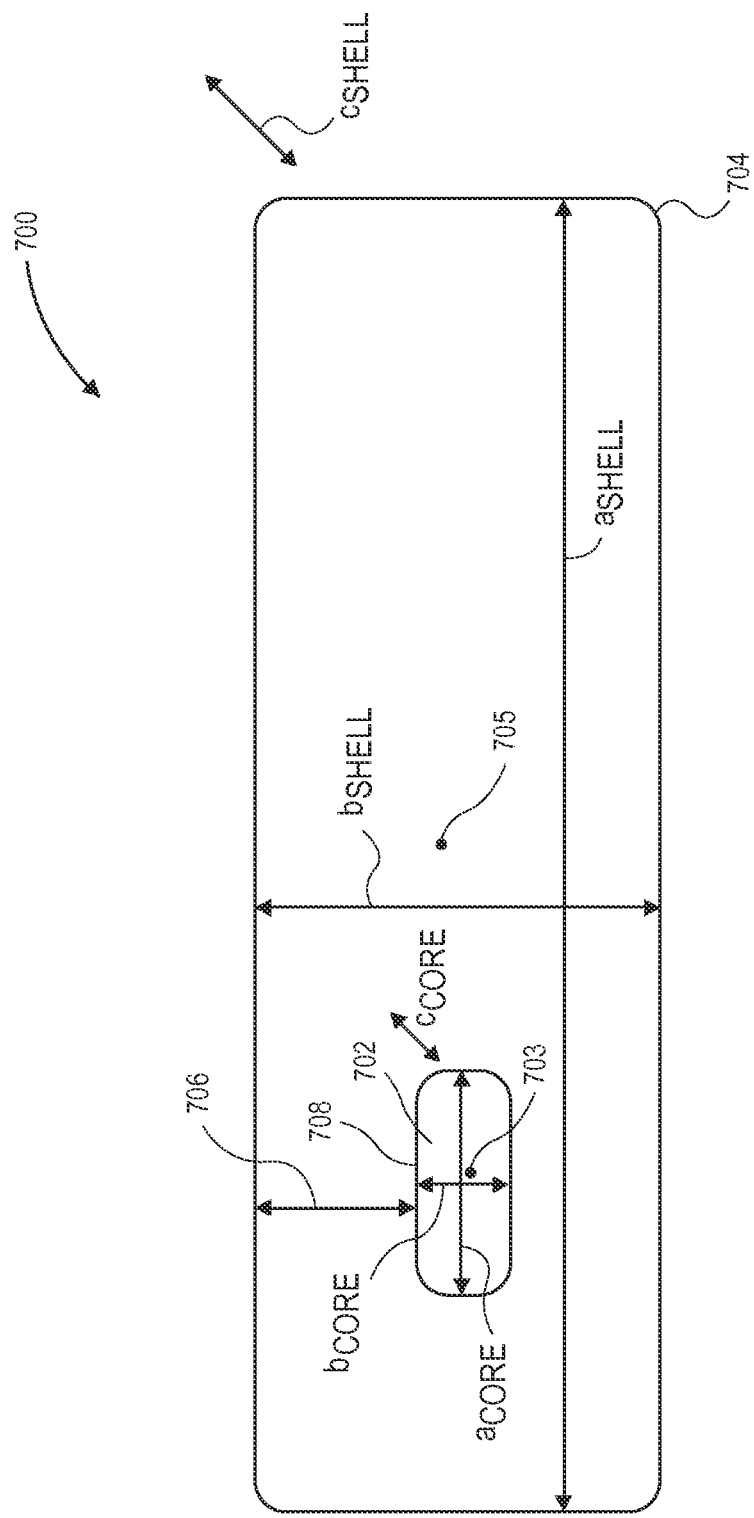
FIG. 7 illustrates a schematic of a cross-sectional view of a quantum dot suitable for delivery by approaches described herein, in accordance with an embodiment of the present invention.

As a reference, FIG. 7 illustrates a schematic of a cross-sectional view of a quantum dot suitable for delivery by approaches described herein, in accordance with an embodiment of the present invention. Referring to FIG. 7, a semiconductor structure (e.g., a quantum dot structure) 700 includes a nano-crystalline core 702 surrounded by a nano-crystalline shell 704. The nano-crystalline core 702 has a length axis ($a_{CORE}$), a width axis ($b_{CORE}$) and a depth axis ($c_{CORE}$), the depth axis provided into and out of the plane shown in FIG. 7. Likewise, the nano-crystalline shell 704 has a length axis ($a_{SHELL}$), a width axis ($b_{SHELL}$) and a depth axis ($c_{SHELL}$), the depth axis provided into and out of the plane shown in FIG. 7. The nano-crystalline core 702 has a center 703 and the nano-crystalline shell 704 has a center 705. The nano-crystalline shell 704 surrounds the nano-crystalline core 702 in the b-axis direction by an amount 706, as is also depicted in FIG. 7.

The following are attributes of a quantum dot that may be tuned for optimization, with reference to the parameters provided in FIG. 7, in accordance with embodiments of the present invention. Nano-crystalline core 702 diameter (a, b or c) and aspect ratio (e.g., a/b) can be controlled for rough tuning for emission wavelength (a higher value for providing increasingly red emission). A smaller overall nano-crystalline core provides a greater surface to volume ratio. The width of the nano-crystalline shell along 706 may be tuned for yield optimization and quantum confinement providing approaches to control red-shifting and mitigation of surface effects. However, strain considerations must be accounted for when optimizing the value of thickness 706. The length (a SHELL) of the shell is tunable to provide longer radiative decay times as well as increased light absorption. The overall aspect ratio of the structure 700 (e.g., the greater of $a_{SHELL}/b_{SHELL}$ and $a_{SHELL}/c_{SHELL}$) may be tuned to directly impact PLQY. Meanwhile, overall surface/volume ratio for 700 may be kept relatively smaller to provide lower surface defects, provide higher photoluminescence, and limit self-absorption. Referring again to FIG. 7, the shell/core interface 708 may be tailored to avoid dislocations and strain sites. In one such embodiment, a high quality interface is obtained by tailoring one or more of injection temperature and mixing parameters, the use of surfactants, and control of the reactivity of precursors.

In accordance with an embodiment of the present invention, a high PLQY quantum dot is based on a core/shell pairing using an anisotropic core. With reference again to FIG. 7, an anisotropic core is a core having one of the axes $a_{CORE}$, $b_{CORE}$ or $c_{CORE}$ different from one or both of the remaining axes. An aspect ratio of such an anisotropic core is determined by the longest of the axes $a_{CORE}$, $b_{CORE}$ or $c_{CORE}$ divided by the shortest of the axes $a_{CORE}$, $b_{CORE}$ or $c_{CORE}$ to provide a number greater than 1 (an isotropic core has an aspect ratio of 1). It is to be understood that the outer surface of an anisotropic core may have rounded or curved edges (e.g., as in an ellipsoid) or may be faceted (e.g., as in a stretched or elongated tetragonal or hexagonal prism) to provide an aspect ratio of greater than 1 (note that a sphere, a tetragonal prism, and a hexagonal prism are all considered to have an aspect ratio of 1 in keeping with embodiments of the present invention).

A workable range of aspect ratio for an anisotropic nano-crystalline core for a quantum dot may be selected for maximization of PLQY. For example, a core essentially isotropic may not provide advantages for increasing PLQY, while a core with too great an aspect ratio (e.g., 2 or greater) may present challenges synthetically and geometrically when forming a surrounding shell. Furthermore, embedding the core in a shell composed of a material different than the core may also be used enhance PLQY of a resulting quantum dot.

Accordingly, in an embodiment, a semiconductor structure includes an anisotropic nano-crystalline core composed of a first semiconductor material and having an aspect ratio between, but not including, 1.0 and 2.0. The semiconductor structure also includes a nano-crystalline shell composed of a second, different, semiconductor material at least partially surrounding the anisotropic nano-crystalline core. In one such embodiment, the aspect ratio of the anisotropic nano-crystalline core is approximately in the range of 1.01-1.2 and, in a particular embodiment, is approximately in the range of 1.1-1.2. In the case of rounded edges, then, the nano-crystalline core may be substantially, but not perfectly, spherical. However, the nano-crystalline core may instead be faceted. In an embodiment, the anisotropic nano-crystalline core is disposed in an asymmetric orientation with respect to the nano-crystalline shell, as described in greater detail in the example below.

Another consideration for maximization of PLQY in a quantum dot structure is to provide an asymmetric orientation of the core within a surrounding shell. For example, referring again to FIG. 7, the center 703 of the core 702 may be misaligned with (e.g., have a different spatial point than) the center 705 of the shell 704. In an embodiment, a semiconductor structure includes an anisotropic nano-crystalline core composed of a first semiconductor material. The semiconductor structure also includes a nano-crystalline shell composed of a second, different, semiconductor material at least partially surrounding the anisotropic nano-crystalline core. The anisotropic nano-crystalline core is disposed in an asymmetric orientation with respect to the nano-crystalline shell. In one such embodiment, the nano-crystalline shell has a long axis (e.g., $a_{SHELL}$), and the anisotropic nano-crystalline core is disposed off-center along the long axis. In another such embodiment, the nano-crystalline shell has a short axis (e.g., $b_{SHELL}$), and the anisotropic nano-crystalline core is disposed off-center along the short axis. In yet another embodiment, however, the nano-crystalline shell has a long axis (e.g., $a_{SHELL}$) and a short axis (e.g., $b_{SHELL}$), and the anisotropic nano-crystalline core is disposed off-center along both the long and short axes.

With reference to the above described nano-crystalline core and nano-crystalline shell pairings, in an embodiment, the nano-crystalline shell completely surrounds the anisotropic nano-crystalline core. In an alternative embodiment, however, the nano-crystalline shell only partially surrounds the anisotropic nano-crystalline core, exposing a portion of the anisotropic nano-crystalline core, e.g., as in a tetrapod geometry or arrangement. In an embodiment, the nano-crystalline shell is an anisotropic nano-crystalline shell, such as a nano-rod, that surrounds the anisotropic nano-crystalline core at an interface between the anisotropic nano-crystalline shell and the anisotropic nano-crystalline core. The anisotropic nano-crystalline shell passivates or reduces trap states at the interface. The anisotropic nano-crystalline shell may also, or instead, deactivate trap states at the interface.

With reference again to the above described nano-crystalline core and nano-crystalline shell pairings, in an embodiment, the first and second semiconductor materials (core and shell, respectively) are each materials such as, but not limited to, Group II-VI materials, Group III-V materials, Group IV-VI materials, Group I-III-VI materials, or Group II-IV-VI materials and, in one embodiment, are mono-crystalline. In one such embodiment, the first and second semiconductor materials are both Group II-VI materials, the first semiconductor material is cadmium selenide (CdSe), and the second semiconductor material is one such as, but not limited to, cadmium sulfide (CdS), zinc sulfide (ZnS), or zinc selenide (ZnSe). In an embodiment, the semiconductor structure further includes a nano-crystalline outer shell at least partially surrounding the nano-crystalline shell and, in one embodiment, the nano-crystalline outer shell completely surrounds the nano-crystalline shell. The nano-crystalline outer shell is composed of a third semiconductor material different from the first and second semiconductor materials. In a particular such embodiment, the first semiconductor material is cadmium selenide (CdSe), the second semiconductor material is cadmium sulfide (CdS), and the third semiconductor material is zinc sulfide (ZnS).

With reference again to the above described nano-crystalline core and nano-crystalline shell pairings, in an embodiment, the semiconductor structure (i.e., the core/shell pairing in total) has an aspect ratio approximately in the range of 1.5-10 and, 3-6 in a particular embodiment. In an embodiment, the nano-crystalline shell has a long axis and a short axis. The long axis has a length approximately in the range of 5-40 nanometers. The short axis has a length approximately in the range of 1-5 nanometers greater than a diameter of the anisotropic nano-crystalline core parallel with the short axis of the nano-crystalline shell. In a specific such embodiment, the anisotropic nano-crystalline core has a diameter approximately in the range of 2-5 nanometers. The thickness of the nano-crystalline shell on the anisotropic nano-crystalline core along a short axis of the nano-crystalline shell is approximately in the range of 1-5 nanometers of the second semiconductor material.

With reference again to the above described nano-crystalline core and nano-crystalline shell pairings, in an embodiment, the anisotropic nano-crystalline core and the nano-crystalline shell form a quantum dot. In one such embodiment, the quantum dot has a photoluminescence quantum yield (PLQY) of at least 90%. Emission from the quantum dot may be mostly, or entirely, from the nano-crystalline core. For example, in an embodiment, emission from the anisotropic nano-crystalline core is at least approximately 75% of the total emission from the quantum dot. An absorption spectrum and an emission spectrum of the quantum dot may be essentially non-overlapping. For example, in an embodiment, an absorbance ratio of the quantum dot based on absorbance at 400 nanometers versus absorbance at an exciton peak for the quantum dot is approximately in the range of 5-35.

In an embodiment, a quantum dot based on the above described nano-crystalline core and nano-crystalline shell pairings is a down-converting quantum dot. However, in an alternative embodiment, the quantum dot is an up-shifting quantum dot. In either case, a lighting apparatus may include a light emitting diode and a plurality of quantum dots such as those described above. The quantum dots may be applied proximal to the LED and provide down-conversion or up-shifting of light emitted from the LED. Thus, semiconductor structures according to the present invention may be advantageously used in solid state lighting. The visible spectrum includes light of different colors having wavelengths between about 380 nm and about 780 nm that are visible to the human eye. An LED will emit a UV or blue light which is down-converted (or up-shifted) by semiconductor structures described herein. Any suitable ratio of emission color from the semiconductor structures may be used in devices of the present invention. LED devices according to embodiments of the present invention may have incorporated therein sufficient quantity of semiconductor structures (e.g., quantum dots) described herein capable of down-converting any available blue light to red, green, yellow, orange, blue, indigo, violet or other color. These structures may also be used to downconvert or upconvert lower energy light (green, yellow, etc.) from LED devices, as long as the excitation light produces emission from the structures.

The above described semiconductor structures, e.g., quantum dots, suitable for delivery by approaches described herein may be fabricated to further include one or more compositional transition layers between portions of the structures, e.g., between core and shell portions. Inclusion of such a transition layer may reduce or eliminate any performance inefficiency associated with otherwise abrupt junctions between the different portions of the structures. For example, the inclusion of a compositional transition layer may be used to suppress Auger recombination within a quantum dot structure. Auger recombination events translate to energy from one exciton being non-radiatively transferred to another charge carrier. Such recombination in quantum dots typically occurs on sub-nanosecond time scales such that a very short multi-exciton lifetime indicates non-radiative recombination, while higher nanosecond bi-exciton lifetimes indicate radiative recombination. A radiative bi-exciton has a lifetime approximately 2-4 times shorter than radiative single exciton.

More specifically, as is described in greater detail below in association with FIGS. 8-10, an optimal particle (e.g., quantum dot structure) may have one or more of a high aspect ratio, a large volume relative to other quantum dot hetero-structures, and graded or alloyed transitions between different semiconductor materials. The graded or alloyed transitions can be used to render a compositional and structural transition from one component (such as a quantum dot core) to another component (such as a quantum dot shell) a smooth function rather than a step function. In one embodiment, the terms "graded," "gradient," or "grading" are used to convey gradual transitioning from one semiconductor to another. In one embodiment, the terms "alloy," "alloyed," or "alloying" are used to convey an entire volume having a fixed intermediate composition. In more specific embodiments, core or seed volume is maximized relative to shell volume for a given emission color. A graded or alloyed core/shell transition layer may be included between the two volumes.

Figure 8:
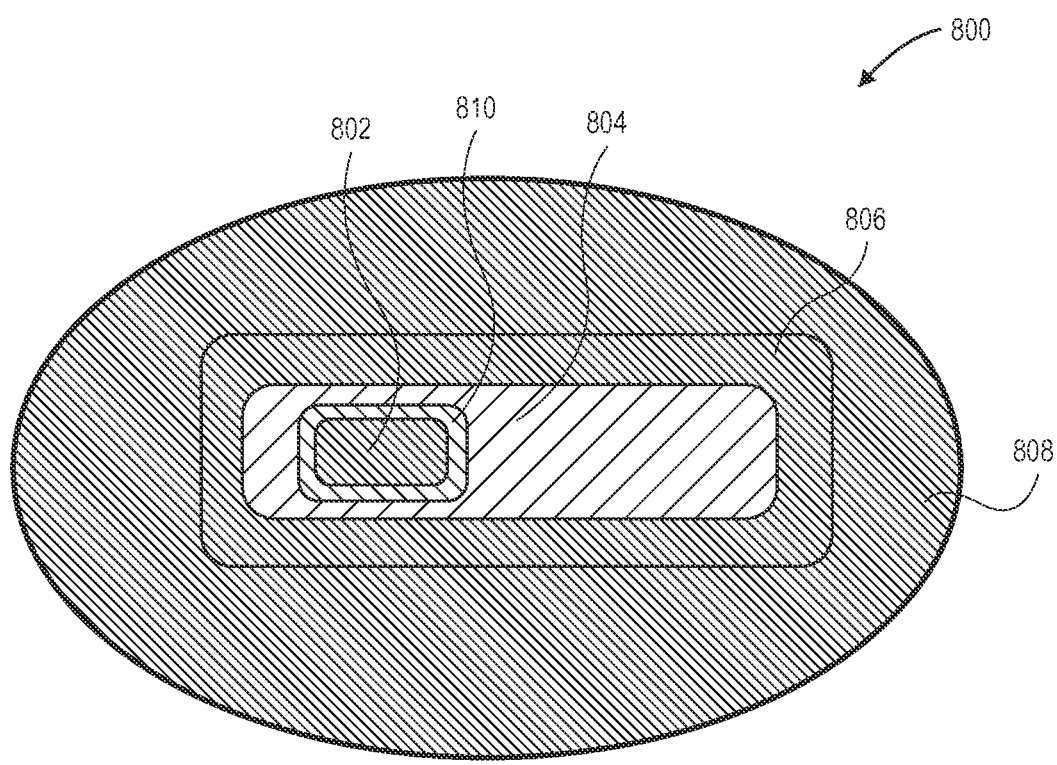
FIG. 8 illustrates a cross-sectional view of a semiconductor structure having a nano-crystalline core and nano-crystalline shell pairing with one compositional transition layer, in accordance with an embodiment of the present invention.

In a first example, FIG. 8 illustrates a cross-sectional view of a semiconductor structure having a nano-crystalline core and nano-crystalline shell pairing with one compositional transition layer, in accordance with an embodiment of the present invention.

Referring to FIG. 8, a semiconductor structure 800 includes a nano-crystalline core 802 composed of a first semiconductor material. A nano-crystalline shell 804 composed of a second, different, semiconductor material at least partially surrounds the nano-crystalline core 802. A compositional transition layer 810 is disposed between, and in contact with, the nano-crystalline core 802 and nano-crystalline shell 804. The compositional transition layer 810 has a composition intermediate to the first and second semiconductor materials.

In an embodiment, the compositional transition layer 810 is an alloyed layer composed of a mixture of the first and second semiconductor materials. In another embodiment, the compositional transition layer 810 is a graded layer composed of a compositional gradient of the first semiconductor material proximate to the nano-crystalline core 802 through to the second semiconductor material proximate to the nano-crystalline shell 804. In either case, in a specific embodiment, the compositional transition layer 810 has a thickness approximately in the range of 1.5-2 monolayers. Exemplary embodiments include a structure 800 where the first semiconductor material is cadmium selenide (CdSe), the second semiconductor material is cadmium sulfide (CdS), and the compositional transition layer 810 is composed of $CdSe_xS_y$, where $0<x<1$ and $0<y<1$, or where the first semiconductor material is cadmium selenide (CdSe), the second semiconductor material is zinc selenide (ZnSe), and the compositional transition layer 810 is composed of $Cd_xZn_ySe$, where $0<x<1$ and $0<y<1$.

In accordance with an embodiment of the present invention, the compositional transition layer 810 passivates or reduces trap states where the nano-crystalline shell 804 surrounds the nano-crystalline core 802. Exemplary embodiments of core and/or shell parameters include a structure 800 where the nano-crystalline core 802 is an anisotropic nano-crystalline core having an aspect ratio between, but not including, 1.0 and 2.0 (in a specific embodiment, approximately in the range of 1.01-1.2), and the nano-crystalline shell is an anisotropic nano-crystalline shell having an aspect ratio approximately in the range of 4-6.

In an embodiment, the nano-crystalline shell 804 completely surrounds the nano-crystalline core 802, as depicted in FIG. 8. In an alternative embodiment, however, the nano-crystalline shell 804 only partially surrounds the nano-crystalline core 802, exposing a portion of the nano-crystalline core 802. Furthermore, in either case, the nano-crystalline core 802 may be disposed in an asymmetric orientation with respect to the nano-crystalline shell 804. In one or more embodiments, semiconductor structures such as 800 are fabricated to further include a nano-crystalline outer shell 806 at least partially surrounding the nano-crystalline shell 804. The nano-crystalline outer shell 806 may be composed of a third semiconductor material different from the first and second semiconductor materials, i.e., different from the materials of the core 802 and shell 804. The nano-crystalline outer shell 806 may completely surround the nano-crystalline shell 804 or may only partially surround the nano-crystalline shell 804, exposing a portion of the nano-crystalline shell 804.

For embodiments including a nano-crystalline outer shell, an additional compositional transition layer may be included. Thus, in a second example, FIG. 9 illustrates a cross-sectional view of a semiconductor structure having a nano-crystalline core/nano-crystalline shell/nano-crystalline outer shell combination with two compositional transition layers, in accordance with an embodiment of the present invention.

Figure 9:
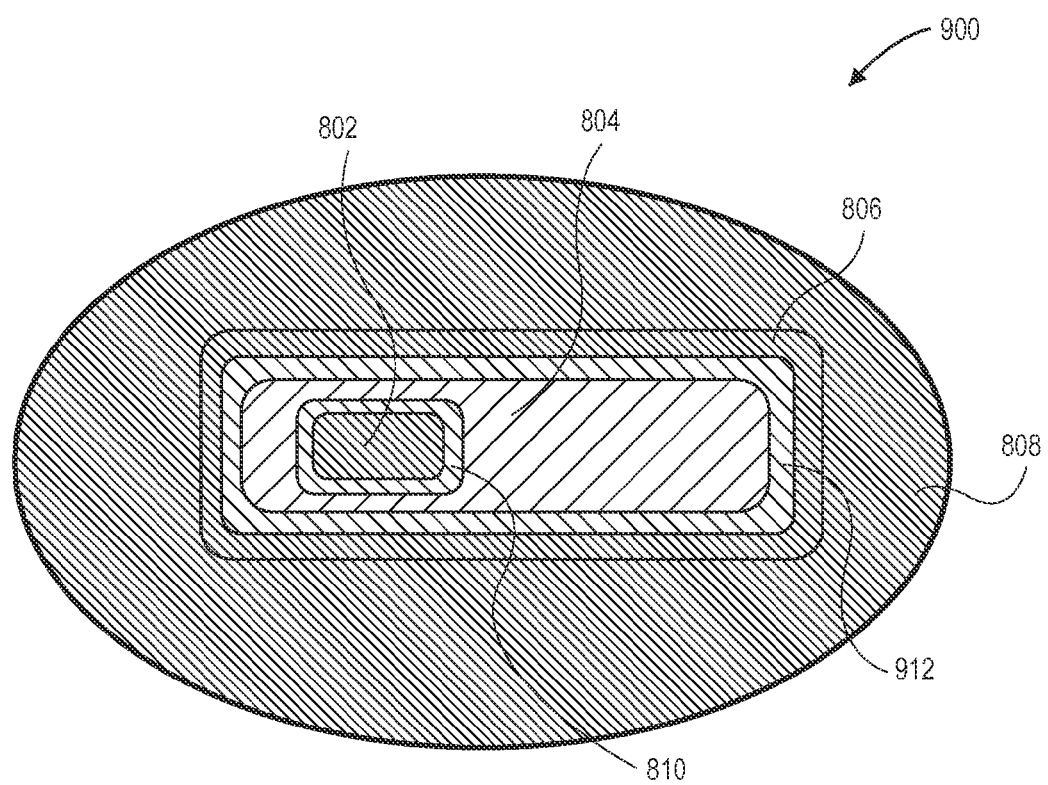
FIG. 9 illustrates a cross-sectional view of a semiconductor structure having a nano-crystalline core/nano-crystalline shell/nano-crystalline outer shell combination with two compositional transition layers, in accordance with an embodiment of the present invention.

Referring to FIG. 9, a semiconductor structure 900 includes the nano-crystalline core 802, nano-crystalline shell 804, nano-crystalline outer shell 806 and compositional transition layer 810 of structure 800. However, in addition, semiconductor structure 900 includes a second compositional transition layer 912 disposed between, and in contact with, the nano-crystalline shell 804 and the nano-crystalline outer shell 806. The second compositional transition layer 912 has a composition intermediate to the second and third semiconductor materials, i.e., intermediate to the semiconductor materials of the shell 804 and outer shell 806.

In an embodiment, the second compositional transition layer 912 is an alloyed layer composed of a mixture of the second and third semiconductor materials. In another embodiment, the second compositional transition layer 912 is a graded layer composed of a compositional gradient of the second semiconductor material proximate to the nano-crystalline shell 804 through to the third semiconductor material proximate to the nano-crystalline outer shell 806. In either case, in a specific embodiment, the second compositional transition layer 912 has a thickness approximately in the range of 1.5-2 monolayers. Exemplary embodiments include a structure 900 where the first semiconductor material is cadmium selenide (CdSe), the second semiconductor material is cadmium sulfide (CdS), the third semiconductor material is zinc sulfide (ZnS), and the second compositional transition layer 912 is composed of $Cd_xZn_yS$, where $0<x<1$ and $0<y<1$, or the first semiconductor material is cadmium selenide (CdSe), the second semiconductor material is zinc selenide (ZnSe), the third semiconductor material is zinc sulfide (ZnS), and the second compositional transition layer 912 is composed of $ZnSe_xS_y$, where $0<x<1$ and $0<y<1$. In accordance with an embodiment of the present invention, the second compositional transition layer 912 passivates or reduces trap states where the nano-crystalline outer shell 806 surrounds the nano-crystalline shell 804.

For other embodiments including a nano-crystalline outer shell, an outer compositional transition layer may be included without including an inner compositional transition layer. Thus, in a third example, FIG. 10 illustrates a cross-sectional view of a semiconductor structure having a nano-crystalline core/nano-crystalline shell/nano-crystalline outer shell combination with one compositional transition layer, in accordance with an embodiment of the present invention.

Figure 10:
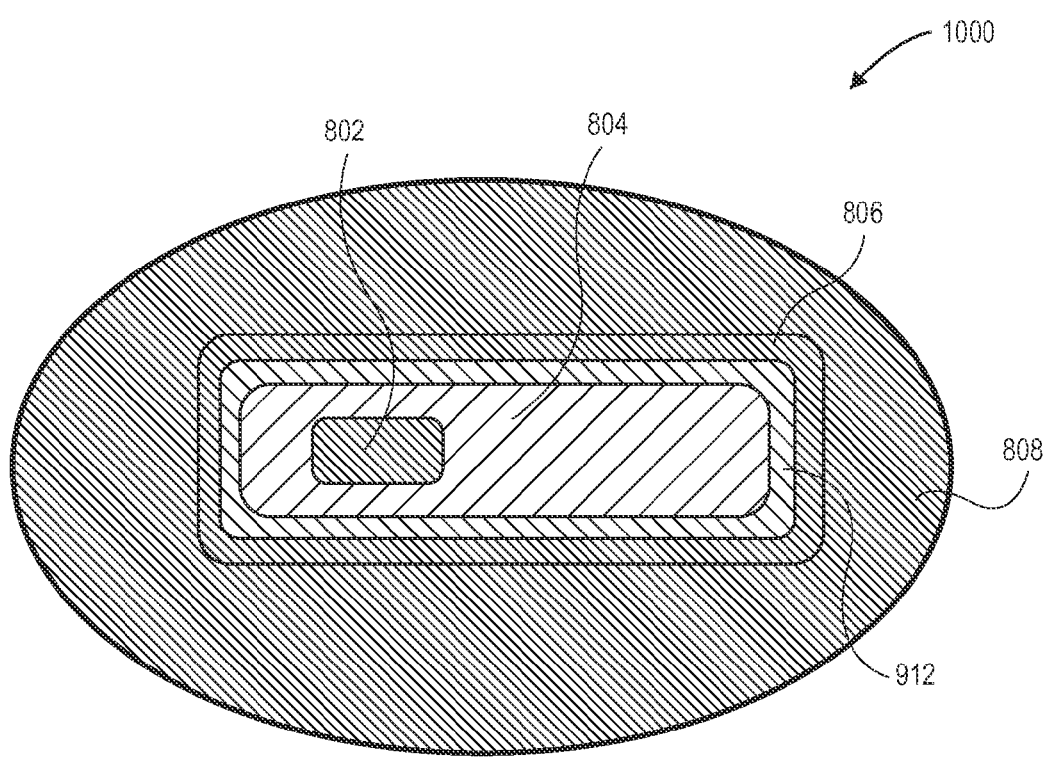
FIG. 10 illustrates a cross-sectional view of a semiconductor structure having a nano-crystalline core/nano-crystalline shell/nano-crystalline outer shell combination with one compositional transition layer, in accordance with an embodiment of the present invention.

Referring to FIG. 10, a semiconductor structure 1000 includes the nano-crystalline core 802, nano-crystalline shell 804, and nano-crystalline outer shell 806 of structure 800. In addition, the semiconductor structure 1000 includes the compositional transition layer 912 of structure 900 disposed between, and in contact with, the nano-crystalline shell 804 and the nano-crystalline outer shell 806. However, structure 1000 does not include the compositional transition layer 810 of structure 800, i.e., there is no compositional transition layer between the core 802 and shell 804.

Referring to FIGS. 7-10, and as depicted in FIGS. 8-10, the structures 700, 800, 900 and 1000 may further include an insulator coating (e.g., shown as 808 in FIGS. 8-10) surrounding and encapsulating the nano-crystalline core/nano-crystalline shell pairing or nano-crystalline core/nano-crystalline shell/nano-crystalline outer shell combination. In one such embodiment, the insulator coating is composed of an amorphous material such as, but not limited to, silica ($SiO_x$), titanium oxide ($TiO_x$), zirconium oxide ($ZrO_x$), alumina ($AlO_x$), or hafnia ($HfO_x$). In an embodiment, insulator-coated structures based on structures 700, 800, 900 and 1000 are quantum dot structures. For example, structures 700, 800, 900 and 1000 may be used as a down-converting quantum dot or an up-shifting quantum dot.

Figure 11:
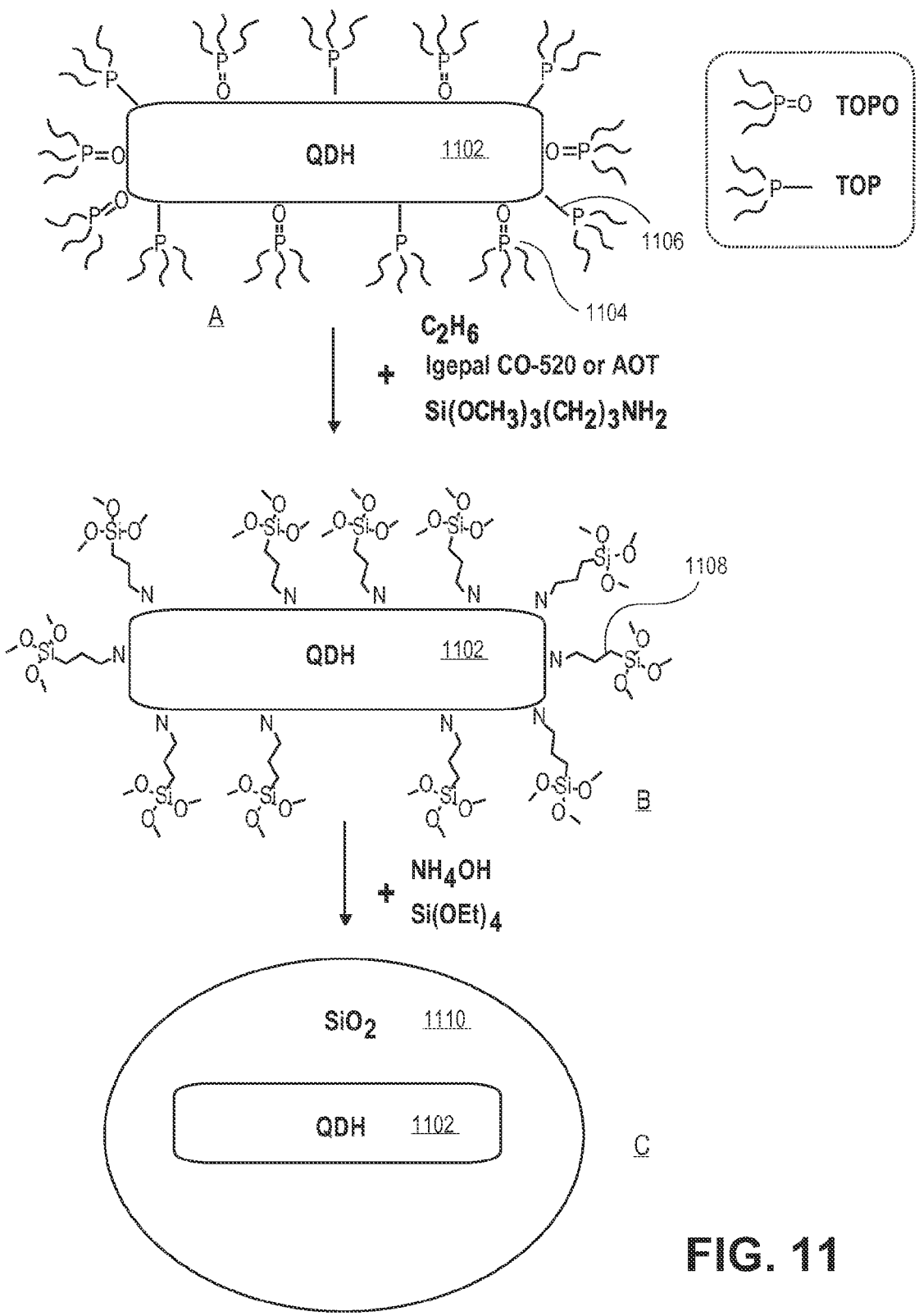
FIG. 11 illustrates operations in a reverse micelle approach to coating a semiconductor structure, in accordance with an embodiment of the present invention.

The above described insulator coating may be formed to encapsulate a quantum dot using a reverse micelle process. For example, FIG. 11 illustrates operations in a reverse micelle approach to coating a semiconductor structure, in accordance with an embodiment of the present invention. Referring to part A of FIG. 11, a quantum dot hetero-structure (QDH) 1102 (e.g., a nano-crystalline core/shell pairing) has attached thereto a plurality of TOPO ligands 1104 and TOP ligands 1106. Referring to part B, the plurality of TOPO ligands 1104 and TOP ligands 1106 are exchanged with a plurality of $Si(OCH_3)_3(CH_2)_3NH_2$ ligands 1108. The structure of part B is then reacted with TEOS ($Si(OEt)_4$) and ammonium hydroxide ($NH_4OH$) to form a silica coating 1110 surrounding the QDH 1102, as depicted in part C of FIG. 11.

In another aspect, nano-particles or quantum dots are delivered by approaches described herein for ultimate use in application for a lighting device, e.g., to provide a layer having a dispersion of semiconductor structures therein for inclusion in the lighting device. In one embodiment, the dispersion of semiconductor structures is a dispersion of quantum dots such as those described above in association with FIGS. 7-11.

Figure 12:
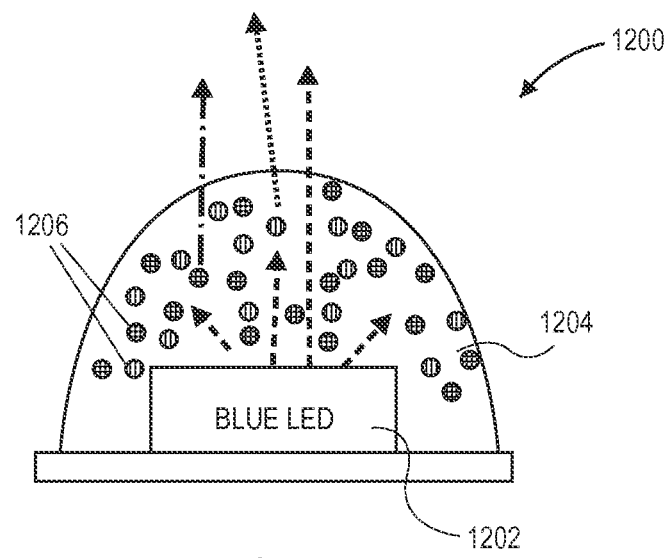
FIG. 12 illustrates a lighting device that includes a blue LED with a layer having a composition with a dispersion of quantum dots therein, in accordance with an embodiment of the present invention.

As an example, FIG. 12 illustrates a lighting device 1200. Device 1200 has a blue LED 1202 with a layer 1204 having a dispersion of quantum dots 1206 therein, in accordance with an embodiment of the present invention. Devices 1200 may be used to produce "cold" or "warm" white light. In one embodiment, the device 1200 has little to no wasted energy since there is little to no emission in the IR regime. In a specific such embodiment, the use of a layer having a composition with a dispersion of anisotropic quantum dots therein enables greater than approximately 40% lm/W gains versus the use of conventional phosphors. Increased efficacy may thus be achieved, meaning increased luminous efficacy based on lumens (perceived light brightness) per watt electrical power. Accordingly, down converter efficiency and spectral overlap may be improved with the use of a dispersion of quantum dots to achieve efficiency gains in lighting and display. In an additional embodiment, a conventional phosphor is also included in the composition, along with the dispersion of quantum dots 1206.

Figure 13:
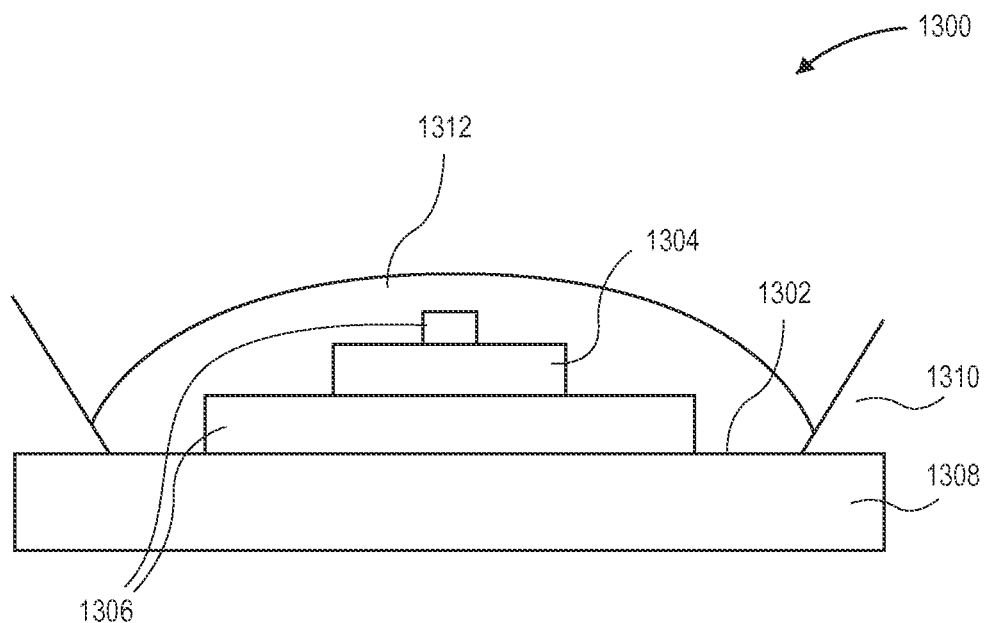
FIG. 13 illustrates a cross-sectional view of a lighting device with a layer having a composition with a dispersion of quantum dots therein, in accordance with an embodiment of the present invention.

Different approaches may be used to provide a quantum dot layer in a lighting device. In an example, FIG. 13 illustrates a cross-sectional view of a lighting device 1300 with a layer having a composition with a dispersion of quantum dots therein, in accordance with an embodiment of the present invention. Referring to FIG. 13, a blue LED structure 1302 includes a die 1304, such as an InGaN die, and electrodes 1306. The blue LED structure 1302 is disposed on a coating or supporting surface 1308 and housed within a protective and/or reflective structure 1310. A layer 1312 is formed over the blue LED structure 1302 and within the protective and/or reflective structure 1310. The layer 1312 has a composition including a dispersion of quantum dots or a combination of a dispersion of quantum dots and conventional phosphors. Although not depicted, the protective and/or reflective structure 1310 can be extended upwards, well above the matrix layer 1312, to provide a "cup" configuration.

Figure 14:
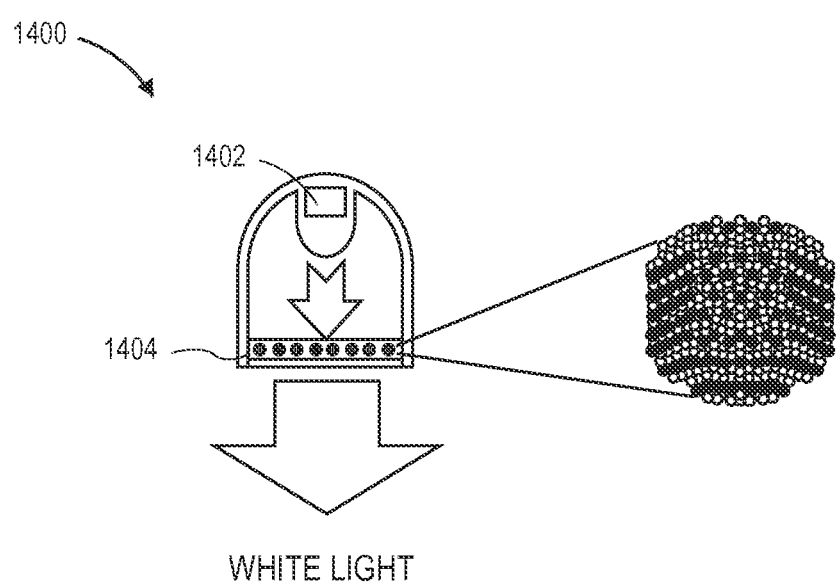
FIG. 14 illustrates a cross-sectional view of a lighting device with a layer having a composition with a dispersion of quantum dots therein, in accordance with another embodiment of the present invention.

In another example, FIG. 14 illustrates a cross-sectional view of a lighting device 1400 with a layer having a composition with a dispersion of quantum dots therein, in accordance with another embodiment of the present invention. Referring to FIG. 14, the lighting device 1400 includes a blue LED structure 1402. A quantum dot down converter screen 1404 is positioned somewhat remotely from the blue LED structure 1402. The quantum dot down converter screen 1404 includes a layer with a composition having a dispersion of quantum dots therein, e.g., of varying color, or a combination of a dispersion of quantum dots and conventional phosphors. In one embodiment, the device 1400 can be used to generate white light, as depicted in FIG. 14.

Figure 15:
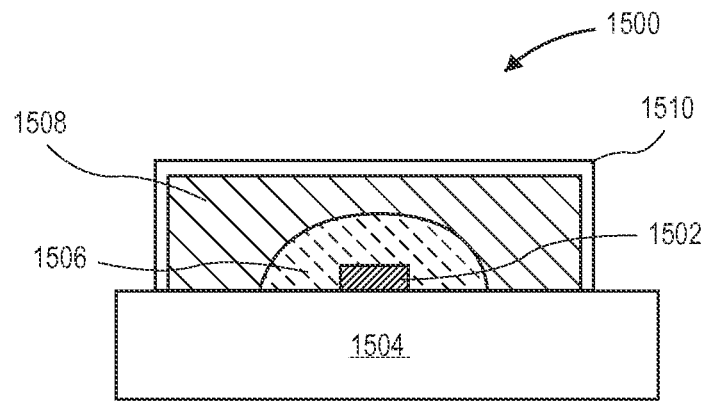
FIG. 15 illustrates a cross-sectional view of a lighting device with a layer having a composition with a dispersion of quantum dots therein, in accordance with another embodiment of the present invention.

In another example, FIG. 15 illustrates a cross-sectional view of a lighting device 1500 with a layer having a composition with a dispersion of quantum dots therein, in accordance with another embodiment of the present invention. Referring to FIG. 15, the lighting device 1500 includes a blue LED structure 1502 supported on a substrate 1504 which may house a portion of the electrical components of the blue LED structure 1502. A first conversion layer 1506 has a composition that includes a dispersion of red-light emitting anisotropic quantum dots therein. A second conversion layer 1508 has a second composition that includes a dispersion of quantum dots or green or yellow phosphors or a combination thereof (e.g., yttrium aluminum garnet, YAG phosphors) therein. Optionally, a sealing layer 1510 may be formed over the second conversion layer 1508, as depicted in FIG. 15. In one embodiment, the device 1500 can be used to generate white light.

Figure 16:
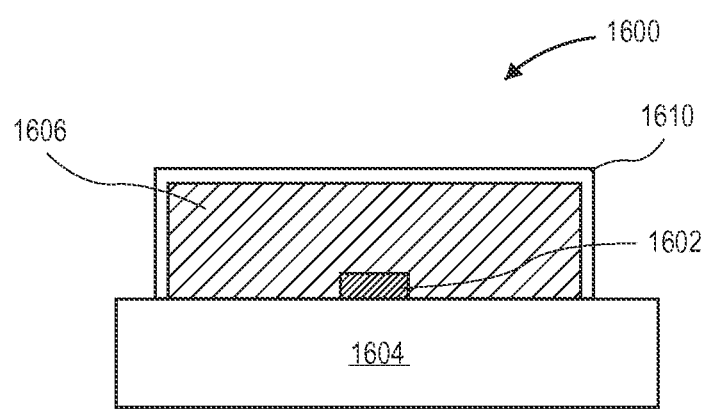
FIG. 16 illustrates a cross-sectional view of a lighting device with a layer having a composition with a dispersion of quantum dots therein, in accordance with another embodiment of the present invention.

In another example, FIG. 16 illustrates a cross-sectional view of a lighting device 1600 with a layer having a composition with a dispersion of quantum dots therein, in accordance with another embodiment of the present invention. Referring to FIG. 16, the lighting device 1600 includes a blue LED structure 1602 supported on a substrate 1604 which may house a portion of the electrical components of the blue LED structure 1602. A single conversion layer 1606 has a composition that includes a dispersion of red-light emitting anisotropic quantum dots in combination with a dispersion of green quantum dots or green and/or yellow phosphors therein. Optionally, a sealing layer 1610 may be formed over the single conversion layer 1606, as depicted in FIG. 16. In one embodiment, the device 1600 can be used to generate white light.

Figure 17A:
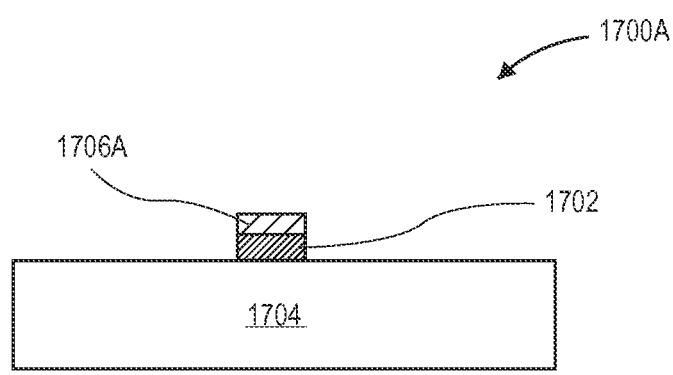
FIGS. 17A-17C illustrate cross-sectional views of various configurations for lighting devices with a layer having a composition with a dispersion of quantum dots therein, in accordance with another embodiment of the present invention.
Figure 17B:
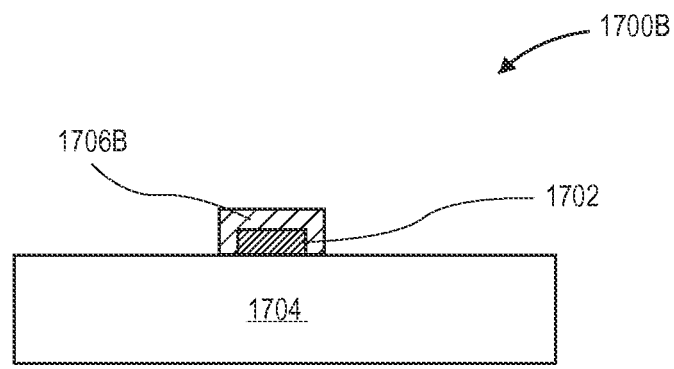
Figure 17C:
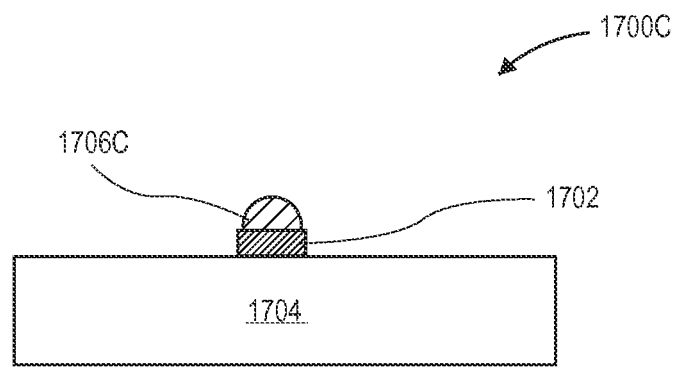

In additional examples, FIGS. 17A-17C illustrate cross-sectional views of various configurations for lighting devices 1700A-1700C with a layer having a composition with a dispersion of quantum dots therein, respectively, in accordance with another embodiment of the present invention. Referring to FIGS. 17A-17C, the lighting devices 1700A-1700C each include a blue LED structure 1702 supported on a substrate 1704 which may house a portion of the electrical components of the blue LED structure 1702. A conversion layer 1706A-1706C, respectively, has a composition that includes a dispersion of one or more light-emitting color types of quantum dots therein. Referring to FIG. 1700A specifically, the conversion layer 1706A is disposed as a thin layer only on the top surface of the blue LED structure 1702. Referring to FIG. 1700B specifically, the conversion layer 1706B is disposed as a thin layer conformal with all exposed surfaces of the blue LED structure 1702. Referring to FIG. 1700C specifically, the conversion layer 1706C is disposed as a "bulb" only on the top surface of the blue LED structure 1702. In the above examples (e.g., FIGS. 12-16 and 17A-17C), although use with a blue LED is emphasized, it is to be understood that a layer having a composition with a dispersion of quantum dots therein can be used with other light sources as well, including LEDs other than blue LEDs.

Figure 18:
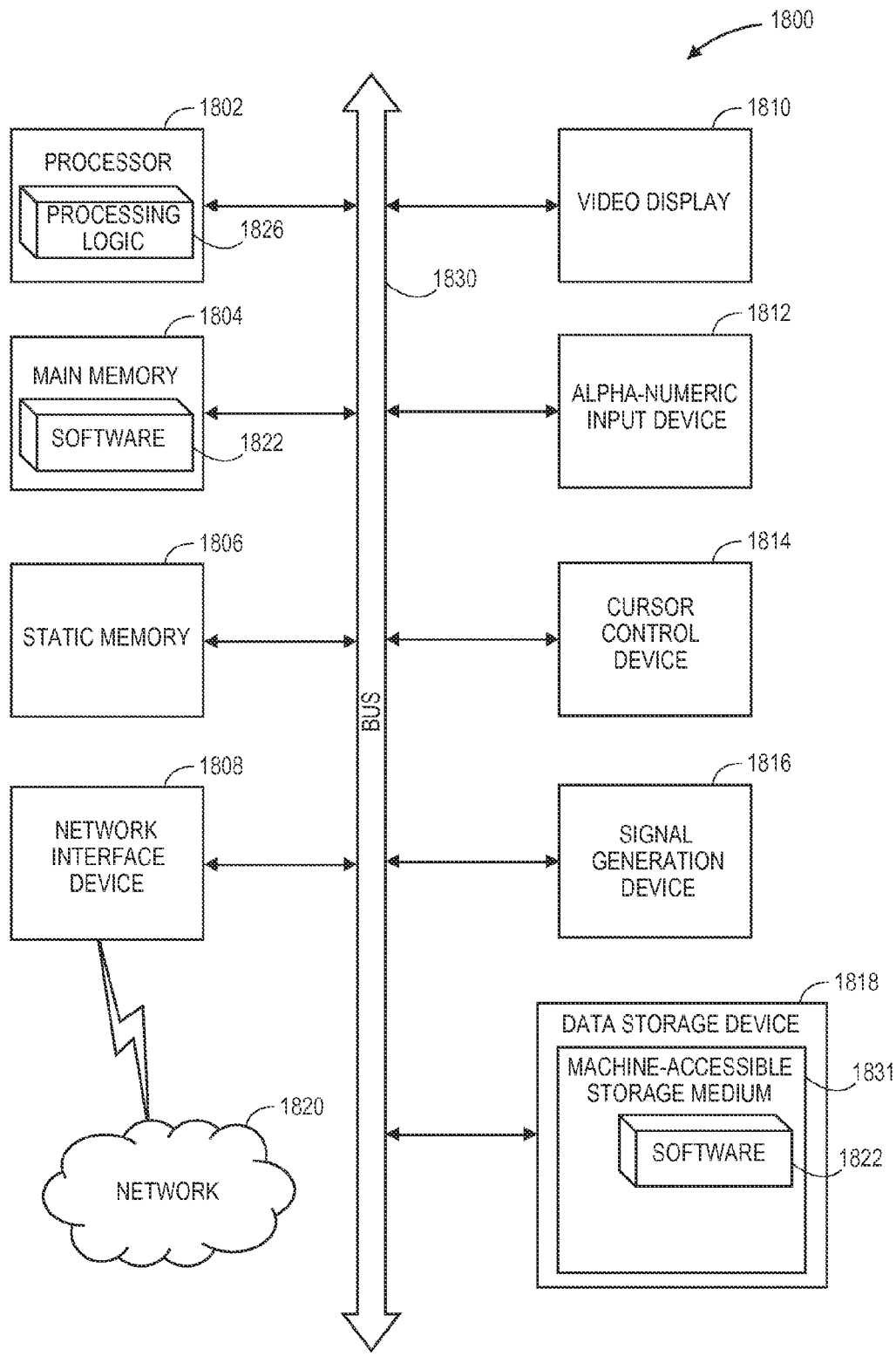
FIG. 18 illustrates a block diagram of an exemplary computer system which controls automated performance of one or more operations in the PLQY testing methods described herein, in accordance with an embodiment of the present invention.

FIG. 18 illustrates a block diagram of an exemplary computer system which controls automated performance of one or more operations in the PLQY testing methods described herein, in accordance with an embodiment of the present invention. The exemplary computer system 1800 includes a processor 1802, a main memory 1804 (e.g., read-only memory (ROM), flash memory, dynamic random access memory (DRAM) such as synchronous DRAM (SDRAM) or Rambus DRAM (RDRAM), etc.), a static memory 1806 (e.g., flash memory, static random access memory (SRAM), etc.), and a secondary memory 1818 (e.g., a data storage device), which communicate with each other via a bus 1830.

Processor 1802 represents one or more general-purpose processing devices such as a microprocessor, central processing unit, or the like. More particularly, the processor 1802 may be a complex instruction set computing (CISC) microprocessor, reduced instruction set computing (RISC) microprocessor, very long instruction word (VLIW) microprocessor, etc. Processor 1802 may also be one or more special-purpose processing devices such as an application specific integrated circuit (ASIC), a field programmable gate array (FPGA), a digital signal processor (DSP), network processor, or the like. Processor 1802 is configured to execute the processing logic 1826 for performing the operations and steps discussed herein.

The computer system 1800 may further include a network interface device 1808. The computer system 1800 also may include a video display unit 1810 (e.g., a liquid crystal display (LCD) or a cathode ray tube (CRT)), an alphanumeric input device 1812 (e.g., a keyboard), a cursor control device 1814 (e.g., a mouse), and a signal generation device 1816 (e.g., a speaker).

The secondary memory 1818 may include a machine-accessible storage medium (or more specifically a computer-readable storage medium) 1831 on which is stored one or more sets of instructions (e.g., software 1822) embodying any one or more of the methodologies or functions described herein. The software 1822 may also reside, completely or at least partially, within the main memory 1804 and/or within the processor 1802 during execution thereof by the computer system 1800, the main memory 1804 and the processor 1802 also constituting machine-readable storage media. The software 1822 may further be transmitted or received over a network 1820 via the network interface device 1808.

While the machine-accessible storage medium 1831 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine-readable storage medium" shall accordingly be taken to include, but not be limited to, solid-state memories, and optical and magnetic media, and other non-transitory machine-readable storage medium.

Thus, photoluminescence quantum yield (PLQY) testing of quantum dots have been disclosed. It is to be understood that the above description is intended to be illustrative, and not restrictive. For example, while flow diagrams in the figures show a particular order of operations performed by certain embodiments of the invention, it should be understood that such order is not required (e.g., alternative embodiments may perform the operations in a different order, combine certain operations, overlap certain operations, etc.). Furthermore, many other embodiments will be apparent to those of skill in the art upon reading and understanding the above description. Although the present invention has been described with reference to specific exemplary embodiments, it will be recognized that the invention is not limited to the embodiments described, but can be practiced with modification and alteration within the spirit and scope of the appended claims. The scope of the invention should, therefore, be determined with reference to the appended claims, along with the full scope of equivalents to which such claims are entitled.

What is claimed is:

1. A method of testing photoluminescence quantum yield (PLQY) of quantum dots, the method comprising:
   heating a sample comprising the quantum dots;
   illuminating the sample with a light source;
   measuring spectra of luminescence from the illuminated quantum dots of the sample at each of a plurality of temperatures;
   measuring each of the plurality of temperatures with a temperature sensor;
   computing the PLQY at each of the plurality of temperatures based on the measured spectra;
   computing a relationship between quantum dot (QD) emission wavelength of the measured spectra and the plurality of temperatures measured with the temperature sensor, wherein computing the relationship between the QD emission wavelength and the plurality of temperatures comprises determining a shift in quantum dot emission peak wavelength with temperature, and wherein determining the shift in quantum dot emission peak wavelength with temperature comprises weighting temperature measurements in a predetermined range to have greater significance in determining the shift; and
   determining a QD temperature corresponding to each of the PLQY computations based on the relationship between the QD emission wavelength and the plurality of temperatures measured with the temperature sensor.

2. The method of claim 1, wherein determining the QD temperature comprises fitting a line to a data set comprising a peak wavelength of the measured spectra at each of the plurality of temperatures and a corresponding measured temperature.

3. The method of claim 1, wherein the predetermined range is 19-65° C.

4. The method of claim 1, further comprising:
   supporting the sample over a stage;
   wherein measuring each of the plurality of temperatures comprises measuring each of the plurality of temperatures with the temperature sensor supported over the stage and adjacent to the sample.

5. The method of claim 4, wherein supporting the sample over the stage comprises:
   supporting the sample over a diffusely reflective solid material; and
   supporting the diffusely reflective solid material with the sample over the stage.

6. The method of claim 4, wherein heating the sample comprises heating the stage over which the sample is disposed.

7. The method of claim 1, further comprising moving an integrating sphere over the sample, wherein:
   illuminating the sample comprises illuminating the sample with the light source coupled with the integrating sphere; and
   measuring the spectra comprises measuring the spectra with a spectrometer coupled with the integrating sphere.

8. The method of claim 7, wherein the integrating sphere is coupled with a gantry, the method further comprising:
   storing coordinates of the sample relative to the gantry;
   while the sample is being heated to a given temperature, moving the integrating sphere on the gantry over another sample comprising quantum dots;
   after taking measurements for the other sample, moving the integrating sphere on the gantry back over the sample based on the stored coordinates; and
   measuring spectra of luminescence from the illuminated quantum dots of the sample at the given temperature without re-positioning the sample.

9. The method of claim 8, wherein the integrating sphere is coupled with a three-axis gantry.

10. The method of claim 7, wherein:
    the light source is coupled with the integrating sphere via a first port; and
    the spectrometer is coupled with the integrating sphere via a second port at 90 degrees relative to the light source.

11. The method of claim 7, wherein illuminating the sample comprises illuminating the sample with a laser or LED.

12. A method of testing photoluminescence quantum yield (PLQY) of quantum dots, the method comprising:
    supporting the sample over a stage;
    heating a sample comprising the quantum dots;
    illuminating the sample with a light source;
    measuring spectra of luminescence from the illuminated quantum dots of the sample at each of a plurality of temperatures;
    measuring each of the plurality of temperatures with a temperature sensor, wherein measuring each of the plurality of temperatures comprises measuring each of the plurality of temperatures with the temperature sensor supported over the stage and adjacent to the sample, wherein the temperature sensor is embedded in a same type of material as the quantum dots;
    computing the PLQY at each of the plurality of temperatures based on the measured spectra;
    computing a relationship between quantum dot (QD) emission wavelength of the measured spectra and the plurality of temperatures measured with the temperature sensor; and
    determining a QD temperature corresponding to each of the PLQY computations based on the relationship between the QD emission wavelength and the plurality of temperatures measured with the temperature sensor.

13. A method of testing photoluminescence quantum yield (PLQY) of quantum dots, the method comprising:
    heating a sample comprising the quantum dots;
    moving an integrating sphere over the sample, wherein the sample is supported over a same diffusely reflective solid material as an interior coating of the integrating sphere;

illuminating the sample with a light source coupled with the integrating sphere;

measuring, with a spectrometer coupled with the integrating sphere, spectra of luminescence from the illuminated quantum dots of the sample at each of a plurality of temperatures;

measuring each of the plurality of temperatures with a temperature sensor;

computing the PLQY at each of the plurality of temperatures based on the measured spectra;

computing a relationship between quantum dot (QD) emission wavelength of the measured spectra and the plurality of temperatures measured with the temperature sensor; and determining a QD temperature corresponding to each of the PLQY computations based on the relationship between the QD emission wavelength and the plurality of temperatures measured with the temperature sensor.

14. A method of testing photoluminescence quantum yield (PLQY) for a plurality of samples comprising quantum dots, the method comprising:

moving an integrating sphere on a gantry over the plurality of samples comprising quantum dots, wherein moving the integrating sphere on the gantry over the plurality of samples is based on stored coordinates of the plurality of samples relative to the gantry;

illuminating a given sample over which the integrating sphere is disposed with a light source coupled with the gantry;

measuring spectra of luminescence from the quantum dots of the given sample at a plurality of temperatures, wherein the integrating sphere moves on the gantry over another sample in between measurements at different temperatures; and computing the PLQY for the plurality of samples at the plurality of temperatures based on the measured spectra.

15. The method of claim 14, wherein:

the light source is coupled with the integrating sphere via a first port; and the spectrometer is coupled with the integrating sphere via a second port at 90 degrees relative to the light source.

16. The method of claim 14, wherein illuminating the given sample comprises illuminating the given sample with a laser or LED.

17. A method of testing photoluminescence quantum yield (PLQY) for a plurality of samples comprising quantum dots, the method comprising:

supporting the plurality of samples over diffusely reflective solid material;

supporting the diffusely reflective solid material with the plurality of samples over one or more stages moving an integrating sphere on a gantry over the plurality of samples comprising quantum dots;

illuminating a given sample over which the integrating sphere is disposed with a light source coupled with the gantry;

measuring spectra of luminescence from the quantum dots of the given sample at a plurality of temperatures, wherein the integrating sphere moves on the gantry over another sample in between measurements at different temperatures; and computing the PLQY for the plurality of samples at the plurality of temperatures based on the measured spectra.

18. The method of claim 17, wherein an interior surface of the integrating sphere comprises a coating of the same diffusely reflective solid material over which the plurality of samples are supported.

19. The method of claim 17, further comprising:

measuring each of the plurality of temperatures with a temperature sensor;

computing the PLQY at each of the plurality of temperatures based on the measured spectra;

computing a relationship between quantum dot (QD) emission wavelength of the measured spectra and the plurality of temperatures measured with the temperature sensor; and determining a QD temperature corresponding to each of the PLQY computations based on the relationship between the QD emission wavelength and the plurality of temperatures measured with the temperature sensor.

20. The method of claim 19, wherein:

computing the relationship between the quantum dot (QD) emission wavelength of the measured spectra and the plurality of temperatures measured with the temperature sensor comprises determining a shift in quantum dot emission peak wavelength with temperature.

21. The method of claim 20, wherein determining the QD temperature comprises fitting a line to a data set comprising a peak wavelength of the measured spectra at each of the plurality of temperatures and a corresponding measured temperature.

22. The method of claim 20, wherein determining the shift in quantum dot emission peak wavelength with temperature comprises weighting temperature measurements in a predetermined range to have greater significance in determining the shift.

23. The method of claim 22, wherein the predetermined range is 19-65° C.

24. The method of claim 17, wherein measuring each of the plurality of temperatures comprises measuring each of the plurality of temperatures with the temperature sensor supported over the one or more stages adjacent to the given sample.

25. The method of claim 24, wherein the temperature sensor is embedded in a same type of material as the given sample.

26. A method of testing photoluminescence quantum yield (PLQY) for a plurality of samples comprising quantum dots, the method comprising:

moving an integrating sphere on a gantry over the plurality of samples comprising quantum dots, wherein the integrating sphere moves over the plurality of samples on a three-axis gantry;

illuminating a given sample over which the integrating sphere is disposed with a light source coupled with the gantry;

measuring spectra of luminescence from the quantum dots of the given sample at a plurality of temperatures, wherein the integrating sphere moves on the gantry over another sample in between measurements at different temperatures; and computing the PLQY for the plurality of samples at the plurality of temperatures based on the measured spectra.

27. A system for testing photoluminescence quantum yield (PLQY) of quantum dots, the system comprising:

a stage to support a sample comprising the quantum dots;

a diffusely reflective solid material disposed over the stage to support the sample;

a heater to heat the sample to a plurality of temperatures;

a light source to illuminate the sample;

a spectrometer to measure spectra of luminescence from the illuminated quantum dots at the plurality of temperatures;

a temperature sensor to measure a temperature of the sample corresponding to the measured spectra; and a computing device to compute:
- the PLQY at the plurality of temperatures based on the measured spectra,
- a relationship between quantum dot (QD) emission wavelength of the measured spectra and the plurality of temperatures measured with the temperature sensor, and
- a QD temperature corresponding to each of the PLQY computations based on the relationship between the QD emission wavelength and the plurality of temperatures measured with the temperature sensor.

28. The system of claim 27, wherein the temperature sensor is supported over the stage and adjacent to the sample.

29. The system of claim 28, wherein the temperature sensor is embedded in a same type of material as the sample.

30. A system for testing photoluminescence quantum yield (PLQY) of a plurality of samples comprising quantum dots, the system comprising:
- an integrating sphere coupled with a gantry;
- an electronic memory to store coordinates of the plurality of samples relative to the gantry, wherein the integrating sphere is configured to move on the gantry over the plurality of samples based on the coordinates;
- a light source coupled with the integrating sphere to illuminate a given sample over which the integrating sphere is disposed;
- a spectrometer coupled with the integrating sphere to measure spectra of luminescence from the given sample at a plurality of temperatures, wherein the integrating sphere is configured to move on the gantry over another sample in between measurements at different temperatures; and
- a computing device to determine the PLQY for the plurality of samples at the plurality of temperatures based on the measured spectra.

31. The system of claim 30, further comprising:
a diffusely reflective solid material disposed over a stage to support the plurality of samples.

32. The system of claim 31, wherein an interior surface of the integrating sphere comprises a coating of the same diffusely reflective solid material over which the plurality of samples are supported.

33. The system of claim 30, wherein the gantry comprises three axes along which the integrating sphere is configured to move.

* * * * *